US012607636B2

(12) United States Patent
Kulkarni et al.

(10) Patent No.: US 12,607,636 B2

(45) Date of Patent: Apr. 21, 2026

(54) CARBENE MASS TAGGING

(71) Applicant: Northeastern University, Boston, MA (US)

(72) Inventors: Pushkar Kulkarni, Allston, MA (US); Roger W. Giese, Hanover, MA (US); Poguang Wang, Westborough, MA (US)

(73) Assignee: Northeastern University, Boston, MA (US)

( * ) Notice: Subject to any disclaimer, the term of this patent is extended or adjusted under 35 U.S.C. 154(b) by 1186 days.

(21) Appl. No.: 17/612,713

(22) PCT Filed: May 22, 2020

(86) PCT No.: PCT/US2020/034176

§ 371 (c)(1), (2) Date: Nov. 19, 2021

(87) PCT Pub. No.: WO2020/237132

PCT Pub. Date: Nov. 26, 2020

(65) Prior Publication Data

US 2022/0244265 A1 Aug. 4, 2022

Related U.S. Application Data

(60) Provisional application No. 62/851,260, filed on May 22, 2019.

(51) Int. Cl.

*G01N 33/58* (2006.01)
*G01N 30/72* (2006.01)

(52) U.S. Cl.

CPC ....... *G01N 33/582* (2013.01); *G01N 30/7233* (2013.01); *G01N 2458/15* (2013.01)

(58) Field of Classification Search

None

See application file for complete search history.

(56) References Cited

U.S. PATENT DOCUMENTS

| | | | |
|---|---|---|---|
| 10,067,136 B1 | 9/2018 | Manetsch et al. | |
| 2004/0115694 A1 | 6/2004 | Van Ness et al. | |
| 2010/0255607 A1 | 10/2010 | Giese | |
| 2020/0041500 A1* | 2/2020 | Kulkarni | G01N 33/54366 |

FOREIGN PATENT DOCUMENTS

WO WO-2020/237132 A1 11/2020

OTHER PUBLICATIONS

CAPLUS printout of U.S. Patent Application Publication No. 2020/0041500 published on Feb. 6, 2020.*

Grant & Hackh's Chemical Dictionary (5th Ed. 1987) at p. 148.*

International Search Report and Written Opinion for International Application No. PCT/US2020/034176 dated Oct. 9, 2020.

* cited by examiner

*Primary Examiner* — Po-Chih Chen

(74) *Attorney, Agent, or Firm* — Foley Hoag LLP; Dana M. Gordon; Tatiana P. Headrick

(57) ABSTRACT

The disclosure relates to a diazirine precursor mass tag compound represented by structural formula (I)

(I)

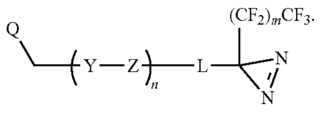

Also disclosed is a method for detecting analytes in a sample, comprising derivatizing the analytes with the compound of formula (I), and detecting the resulting derivatized analytes by a mass or ion mobility spectrometry.

20 Claims, 23 Drawing Sheets

Detection of Acebutolol by MALDI-TOF MS after tagging with CAX-DZ : capillary vial experiment

Acebutolol

| UV time (min) | SM (Area) | Product (Area) | Yield Ratio |
|---|---|---|---|
| 0 | 20149 | 0 | 0 |
| 60 | 4041 | 15961 | 0.797 |
| 60 | 6250 | 15308 | 0.710 |
| 60 | 5899 | 16392 | 0.735 |
| 60 | 9355 | 22095 | 0.702 |

SIM (m/z 608)
of Tagged Acebutolol

CARBENE MASS TAGGING

RELATED APPLICATIONS

This application is a U.S. National Stage Application of International Application No. PCT/US20/34176, filed May 22, 2020; which claims the benefit of priority to U.S. Provisional Patent Application No. 62/851,260, filed May 22, 2019.

GOVERNMENT SUPPORT

This invention was made with government support under Grant Number ES017198, awarded by the National Institutes of Health. The government has certain rights in the invention.

BACKGROUND

Methods for chemical analysis of small organic molecules (such as metabolites, pollutants, small drugs, and natural products) in complex samples by mass spectrometry (MS) or ion mobility spectrometry (IMS) are limited in one or more of the following overlapping respects: incomplete detection; slow; expensive; steps requiring high temperature; poor sensitivity; limited scope (multiple procedures and/or instrumentation needed to detect all of the substances of interest in sample); weak capability for discovery analysis, and low specificity (inability or limited ability to discriminate related analytes or to distinguish signal from noise). Incomplete detection means that only some of the compounds present in a sample are detected because amounts of other compounds are very low; they give a poor response in MS or IMS; or both. Methods are slow when one or more steps of the procedure is slow, such as a multi-hour derivatization reaction. While a mass spectrometer is expensive, it is a one-time cost, and other sources of cost become more important in practice such as expensive reagents/supplies, or multiple analytical steps that require much time by the analyst. High temperature treatment tends to decompose many analytes while increasing side reactions that, in turn, increase noise and thereby lower sensitivity. Sensitivity can be poor because many compounds do not give a high response in the mass spectrometer. There are compounds which can be detected by electrospray mass spectrometry (usually coupled to liquid chromatography; LC-MS), but not by electron impact mass spectrometry (usually coupled to gas chromatography). While triple quadrupole mass spectrometers can provide high sensitivity, this is only true for some known compounds so that detection by single ion monitoring can be employed. A good example of the need for multiple mass spectrometers is in the analysis of cannabis products for cannabinoids, terpenes, solvents, and pesticides. An LC-MS instrument normally is used to detect cannabinoids; a GC-MS instrument is normally used to detect the terpenes; and then different conditions are used on the LC-MS to detect the cannabinoids vs the pesticides. Thus each method is limited in its scope. Overall this gives a slow, complex, and expensive analysis for cannabis. Determination of the overall organic chemical composition of a complex sample by a single method is of interest for several areas such as clinical and drug diagnostics, metabolomics, environment, foods and food safety, manufacturing, forensics, surveillance, and homeland security. However, multi-class, broad scope chemical analysis by a single method does not exist.

Achieving high specificity is very important in chemical analysis, such as by liquid chromatography mass spectrometry (LC-MS), a leading technique for achieving specificity in chemical analysis. Low specificity is a major problem of IMS. Specificity refers to the ability to report exactly what chemical is producing a chromatographic, mass spectral, or mobility peak of interest. In other words, it refers to the ability to identify a peak with high or complete certainty. Since there is a vast number of chemicals, it is often difficult to be absolutely sure about the identity of a detected chemical. For example, a given mass spectral peak may be formed by different isobars (chemicals with the same nominal mass but different molecular compositions). While detection of a peak with a very high resolution mass spectrometer may overcome this problem, the problem gets worse for chemicals with higher masses, and it can take much effort to measure a molecular mass accurately. Isomers present a similar problem. Since isomers have the same molecular formula, a high resolution mass spectrometer can be of no help in truly learning isomeric identity, and isomers can also have the same chromatographic retention time or mobility.

The problem of identifying (annotating) peaks, also known as a specificity challenge, especially plagues the field of metabolomics by mass spectrometry. A very large number of chromatographic and mass spectral peaks is commonly seen when metabolomic analysis is done by LC-MS. To annotate a metabolite peak, a common strategy is to measure three features of the peak: (1) the LC retention time, (2) the mass of the precursor ion (which can be also called the molecular ion), and (3) the fragmentation pattern in MS2. With all of this information, one then searches a library (list) of known compounds for which such data are available, and tries to find a compound there with matching peak parameters (retention time, molecular ion, fragment ion pattern). Unfortunately, retention times are limited in their reproducibility; a measured mass may only be close to the true (accurate) mass; fragmentation patterns are instrument-dependent; some molecular ions give few fragment ions; chemical noise can give faulty mass values for ions of interest; and it may not be clear which ions are fragment ions and which are noise when only a small amount of a chemical is being tested.

In spite of its low specificity, IMS is very popular since it is convenient, compact, and relatively inexpensive. Such instruments are commonly used to check luggage at airports for explosives and narcotics (where the luggage is rubbed with a swab, and the swab then is inserted into an IMS instrument). However, the low specificity of IMS severely compromises its performance. This specificity problem is a great frustration for Homeland Security where explosives, drugs of abuse, and warfare agents need to be detected with high certainty. Using a mass spectrometer instead of an IMS at airports is not an adequate solution since mass spectrometers are expensive complicated instruments requiring skilled operators. While simpler mass spectrometers are emerging, they have reduced resolution, specificity, and sensitivity. The complication problem increases when the mass spectrometer is part of an LC-MS system. Combining IMS with MS at the airport is not a practical remedy either.

In mass tag mass spectrometry (MTMS), analytes are derivatized with a reagent termed a "mass tag" usually to increase sensitivity. A cation-prone group (secondary or tertiary amine that readily protonates), or a permanently cationic group such as a quaternary amine, is usually selected to give the high sensitivity. For the reactive part, a functional group capable of labeling the analyte(s) of interest is selected.

While carbenes are known as a type of reactive group, they have not been incorporated into mass tags. Instead, carbenes have been used for affinity labeling (Das, J. [2011] Aliphatic Diazirines as Photoaffinity Probes for Proteins: Recent Development, Chemical Reviews, 111, 4405-4417; Hill, J. R., Robertson, A. A. B. [2018] Fishing for Drug Targets: A Focus on Diazirine Photoaffinity Probe Synthesis, J. Med. Chem. 61, 6945-6963; footprinting/mapping (Ziemianowicz, D. S, Bomgarden, R., Etienne, C. and Schriemer, D. C. [2017] Amino Acid Insertion Frequencies Arising from Photoproducts Generated Using Aliphatic Diazirines, J. Am. Soc. Mass Spectrometry, 2011-2021); and fabrication (J. de Zwart, F., Bootsma, J., de Bruin, B. [2019] Science 366, 800-805).

SUMMARY

In certain aspects, the present disclosure relates to a diazirine precursor mass tag compound represented by structural formula (I)

(I)

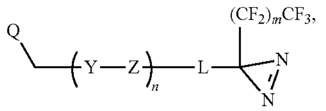

wherein, independently for each occurrence,

Q is $-NR^6R^7$, $-(NR^6R^7R^8)^+X^-$, pyridyl, or

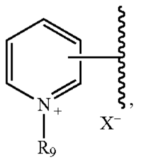

X is Hal, $NO_3$, $OC(O)CH_3$, $OC(O)C(CH_3)_3$, $OC(O)CF_3$, $HCO_3$, $AsO_2$, $H_2AsO_4$, $AsF_6$, $SO_3(C_4F_9)$, $SO_3(C_6F_{13})$, $SO_3C_8F_{17}$, $ClO_4$, CN, $BF_4$, $SnCl_3$, $CF_3SO_3$, or $C_6F_5O$;

$R^6$, $R^7$, $R^8$ is each independently $C_{1-6}$ alkyl or $C_{6-10}$ aryl;

$R^9$ is $C_{1-3}$ alkyl;

Y is $C_{6-10}$ aryl or 5-membered to 9-membered heteroaryl;

Z is $-(CH_2)_lA(CH_2)_k-$;

L is $-(CH_2)_lA(CH_2)_k-$ or absent;

A is O, S, or NH;

l is 0 to 2;

k is 0 to 2;

m is 0 to 10; and n is 1 to 3.

In certain aspects, the present disclosure relates to a method for detecting one or more analytes in a sample, comprising:

a) combining the sample and a reagent mixture, wherein the reagent mixture comprises a diazirine precursor mass tag reagent, and wherein the diazirine precursor mass tag reagent is a compound of formula (I), thereby generating an analyte mixture;

b) exposing the analyte mixture to a source of energy, thereby providing derivatized analyte mixture; and c) analyzing the one or more derivatized analytes, thereby detecting the one or more analytes.

DETAILED DESCRIPTION

Figure 1:
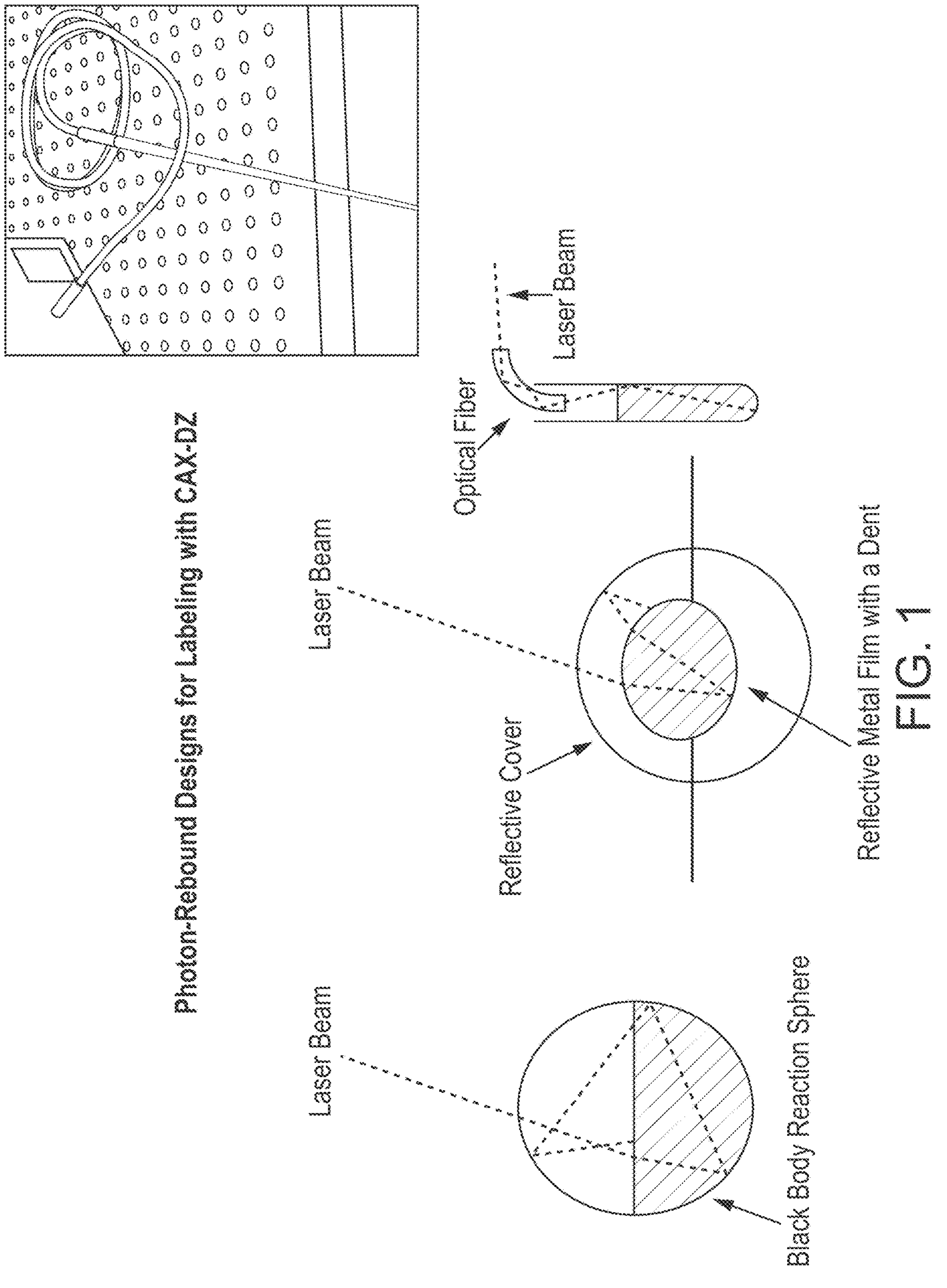
FIG. 1 shows a schematic representation of the concept of creating rebounded photons via the black body principle to increase speed and yield of CAX-DX labeling of analytes

The present disclosure relates to Carbene Mass Tagging (CMT) technology which allows to overcome the problems of sensitivity, scope, and specificity in chemical. CMT technology involves covalently modifying the sample of interest with the carbene group of a carbene-bearing mass tag reagent (CMT reagent) having a cation-prone group (secondary or tertiary amine) or cationic group (quaternary amine, pyridinium, or phosphonium) followed by detection by MS or IMS. The cation-prone or cationic group enhances sensitivity for detection by MS or IMS. The cationic group can be a quaternary amine group, such as a quaternary amine group bearing a benzyl moiety. The carbene group is generated through energetic activation of the diazirine group of a diazirine precursor mass tag. This activation is done in the presence of the sample to be labeled, or just prior to combining the diazirine precursor mass tag with the sample.

CMT also enhances the scope of detection of chemical analytes due to the broad reactivity of carbenes. Cation-prone or cationic labeling of organic compounds in a sample is achieved in a more comprehensive way than any of the presently used methods. The carbene labeling reaction also is fast, helping to make CMT practical. For example, CMT technology allows for detection by LC-MS of compound that have only or usually been detected by GC-MS, so a single procedure accomplishes the analysis of multiple classes of compounds. The CMT technology is not only practical, but is a powerful tool for discovery analysis. Furthermore, compounds labeled by CMT tend to be sensitive to electrospray ionization mass spectrometry, MALDI mass spectrometry, and ion mobility spectrometry CMT can be used to profile chemicals with broad scope in a great diversity of samples, such as the following: blood, urine, breath, saliva, sweat, tears, hair, skin, skin lesions (e.g. suspected melanoma), tissues, ear wax, feces, vomit, foods, meats, vegetables, metabolites, fruits, plants, beverages, aromas, odors, fabrics, clothing, dust, surfaces, soils, drinking water, paints, creams, drugs, papers, wipes from surfaces, leaves, barks, fragrances, cosmetics, soots, particles, extracts, smoke, vapor, roots, water, organic solvents, teas, coffee, cooking sprays, cannabis, spices, flavorings, fragrances, plastics, polymers, glues, sauces, vehicle exhaust, bombs, bomb residues, fingerprints, powders, oils, cleaners, personal hygiene products, natural products, nutraceutical products, pollutants, muds, powders, microorganisms, cell culture, body fluids, and biological tissues. The CMT reagents can be used in footprinting experiments of macromolecules such as proteins and nucleic acids.

CMT can be used for other purposes, such as: (1) give a nonpolar plastic surface a polar coating; (2) make a nonpolar plastic surface adhesive towards a complementary surface or particle bearing a negative charge; (3), install a polar spot on a nonpolar surface to focus a spot of sample in a MALDI-TOF/TOF-MS experiment; (4) provide a surface that captures small particles such as cells, dust, parasites, viruses or other microorganisms; (5) provide a surface that captures nucleic acids or proteins; (6) provide a surface for chromatographic purposes; (7) provide a surface for reaction purposes such as an immobilized quaternary amine with a hydroxide counter ion for hydroxylation reactions or for alkylation of NH, OH, or SH sites on molecules; (8) create spots of molecular diversity for electronic noses and affinity chromatography by modifying prior surface molecules in a diversity of ways; (9) expand the diversity of a library of compounds to be screened as drugs; (10) identify an unknown compound, where the viper signature (see below) of the unknown compound and the viper signature of a known compound match, confirming identity, and this can be done at a trace level; and (11) help to identify an unknown compound, where its viper signature is similar to that of some known compound, or the observed viper signature for the unknown compound is compared theoretically with those calculated from known compounds or a library of theoretical structures. These applications can benefit from the viper reactivity of a quaternary amine CMT mass tag, where the carbene group attacks each target molecule only once due to charge repulsion, and each of the prominent parts of the target molecule is attacked, giving a family of monolabeled, isomeric products.

CMT also increases specificity of chemical analysis, while retaining high sensitivity, for both LC-MS and IMS. This is accomplished by relying on the "viper-like" reactivity of a CMT reagent in the carbene form. Just as a viper snake strikes any prominent part of a victim, the carbene group of a CMT reagent can insert into more than one bond of an analyte compound of interest. Each analyte molecule (unless it is very large) is labeled once because of subsequent charge repulsion, yielding a family of mono-labeled isomers which tend to give a pattern of peaks (signature) when a mobility or chromatographic separation is done. This signature depends on the relative reactivity of the bonds in the analyte compound towards the carbene reagent. While a carbene can insert into a diversity of chemical bonds, most the frequent site of insertion is an X—H bond, where X is O, N, S, or C. Stereoisomers of target analytes can give different mixtures of labeled products. Moreover, enantiomers of a given compound can give different signatures when a chiral carbene reagent is employed. This, in turn, leads to a unique pattern of peaks (a "signature") when the product mixture is analyzed by LC-MS or IMS. For example, ethanol can give three peaks in distinctive pattern unmatched by any other molecule, from labeling each of its three types of its XH bonds: OH, $CH_2$, and $CH_3$.

Another benefit from single labeling of an analyte (at different sites) by using a cationic carbene reagent is that all of the products are isomers and thereby give the same molecular ion by matrix-assisted laser desorption ionization mass spectrometry or flow injection (infusion) mass spectrometry, which lack a stage of separation prior to entry into the mass spectrometer.

For the cationic group, a quaternary amine is well suited for viper labeling since it tends to give monolabeling of a target compound. Once a given target compound is labeled with such a reagent, the positive charge of the product repels other quaternary amine carbene reagents from attaching (unless the target compound is very large). Monolabeling of the target prevents the signature (fingerprint) pattern of peaks from becoming overly complex. The problem with a highly complex pattern of peaks is the potential loss in sensitivity, since each product peak has a lower height than the parent peak. However, high levels of complexity can be acceptable since a compound having a quaternary amine group tends to be ultrasensitive for detection by mass spectrometry, which can make up for the loss in sensitivity when an original, single peak for an analyte is converted into a pattern of peaks by the carbene derivatization reaction.

The quaternary amine group in the carbene reagent can be a pyridinium ion. Cation-prone groups include picolinoyl, pyridinoyl, and 3-aminopyridyl groups. A phosphonium group, such as tris(2,4,6-trimethoxyphenyl)phosphonium, can provide the positive charge of a cationic CMT reagent.

Having a tertiary or a secondary amine in a CMT reagent permits the carbene-labeled compound to readily undergo thermal desorption, a common method for introducing a compound into an IMS or MS instrument, especially when the sample is on a swab, as at an airport or border security station.

The degree of signature formation for an analyte via CMT can be controlled by varying the steric bulk of the carbene reagent. Sterically bulky carbene reagents tend to be more selective in the labelling process due to a buildup of steric, dipole, van der Waals or other noncovalent interactions with the target analyte of interest. For example, to increase the steric bulk of the CMT reagent, one could substitute a $CF_3$ group on a $CF_3$-substituted diazirine group of the diazirine precursor mass tag with a larger polyfluorinated group such as $C_2F_5$, $C_3F_7$, $C_4F_9$, etc, in order to avoid an excessively complex labeling signature that can compromise sensitivity.

Sensitivity of the CMT technology can be increased by adding a scavenging agent to react with the residual diazirine reagent upon activation of the latter to carbene. The procedure involves adding the scavenger agent after sufficient analyte has been labeled, and then proceeding to activate the residual diazirine reagent to a carbene for reaction with the scavenger agent. A scavenging agent is an insoluble or poorly soluble compound bearing an OH, NH, or CH groups, such as silica, agarose, chitin, dextrin, pectin, polyethylene glycol, polyacrylamide, ethylenediamine-substituted polyacrylamide, Ficoll™, cellulose, paper, nylon, albumin, a dendrimer, Sephadex™, polymethacrylate, polyvinylchloride, polyvinylpyrollidone, cellulose acetate, a polypeptide, a carbohydrate (such as sucrose), diamines (such as 1,8-diaminooctane), collagen, a triglyceride, lecithin, a dihydrazide, or glucocerebroside.

The carbene-conjugated forms of the of scavenging agents (formed in the scavenging reaction) can be removed by one or more of the following techniques: filtration, centrifugation, magnetic attraction, precipitation, adsorption, absorption, liquid or solid phase extraction, liquid chromatography, or size exclusion chromatography. A scavenging agent substituted with one or multiple biotin groups can be used, allowing for removal of the carbene-conjugated agent on a streptavidin column. A scavenging agent substituted with one or multiple ligands for a commercial molecular imprinted polymer (MIP) can be used, for the removal of the carbene-conjugated agent on a corresponding MIP column. When the scavenger is glucocerebroside, carbene-conjugated glucocerebroside can be removed on a C18-substituted silica chromatography column or OASIS™ column. A dihydrazide can be used as a scavenger, since a carbene-conjugated dihydrazide can be removed on an aldehyde column. Sucrose or a larger sugar can be used as a scavenger, since residual carbene-conjugated sucrose can be removed on a hydrophilic interaction chromatography column. Dimers of MIP ligands can be used, since the carbene-conjugated dimer can be removed on a MIP column. Diamines such as 1,8-diaminooctane can be used as a scavenger, since carbene-conjugated diamine can be removed on an N-hydroxysuccinimide column.

The carbene labeling reaction can be conducted in the liquid phase comprising a solvent such as a nitrile (e.g., acetonitrile), water, an alcohol such as methanol; an ester such as ethyl acetate; an ether such as diethyl ether or t-butylmethyl ether; a hydrocarbon such as octane or toluene; a polyhalogenated compound such hexafluorobenzene, octafluorotoluene, dichloromethane, or trifluoromethyl trifluoroacetate; an ionic liquid; or a liquid containing micelles. The carbene labeling reaction can take place in the gas phase. The carbene reaction can be conducted on a solid surface such as glass, paper, Teflon™ (polytetrafluoroethylene), ice, plastic, quartz, ceramic, metal, or sulfopolystyrene by coating the solid phase with both a diazirine mass tag and the analyte, and applying energy to activate the diazirine reagent to the corresponding carbene reagent. This surface can be clean or contain a thin film of solvent or oil or wax or paint. The carbene labeling reaction can be conducted within a solid phase, including a solid phase formed at a low temperature and containing both the CMT diazirine reagent and the analyte. This solid phase can be amorphous, crystalline, or glass.

The energy which converts the diazirine group on the diazirine precursor mass tag to a carbene group can be furnished by a UV photon, as from a laser or light-emitting diode (LED), a heat photon, a metastable ion or molecule, an electronically-excited dye that transfers the energy by fluorescence energy transfer, a plasma, a fast atom or ion, a vibrationally-activated ion or molecule that transfers its energy to the diazirine mass tag (as via a collision), electricity, or a reactive molecule such as ozone, an ozonide, or a peroxide including a diacylperoxide especially at an elevated temperature.

The carbene labeling reaction, including activation of the corresponding diazirine reagent to the carbene, can be conducted in a glass container enshrouded in mirror finished or reflective metal such as aluminum foil or stainless steel, or in a vessel or tube made of metal. In certain embodiments, the reaction is conducted by exposing the reaction mixture to LED photons through the wall of a glass or plastic tube (UV transparent at 350 nm) that are collimated to arrive at this surface tangent plane at a right angle.

As used herein, the term "$C_{x-y}$", when used in conjunction with a chemical moiety, such as, acyl, acyloxy, alkyl, alkenyl, alkynyl, or alkoxy is meant to include groups that contain from x to y carbons in the chain. A $C_{1-6}$ alkyl group, for example, contains from one to six carbon atoms in the chain.

As used herein, the term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "aryl" as used herein include substituted or unsubstituted single-ring aromatic groups in which each atom of the ring is carbon. For example, the ring is a 6—to 10-membered ring, such as a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "diazirine", is art-recognized and may be represented by the general formula

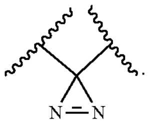

The terms "halo" and "halogen" ("Hal") as used herein means halogen and includes chloro, fluoro, bromo, and iodo.

The term "polyhalogenated hydrocarbon", as used herein, relates to a hydrocarbon, such as an alkane, an alkene, an alkyne, or an arene, in which all hydrogen atoms are replaced with halogens. For example, a polyhalogenated hydrocarbon can by polyfluorinated (all hydrogen atoms are replaced with fluorines), polychlorinated (all hydrogen atoms are replaced with chlorines), or polybrominated (all hydrogen atoms are replaced with bromines).

The terms "heteroaryl" includes substituted or unsubstituted aromatic single ring structures, whose ring includes at least one heteroatom (such as O, N, or S). A heteroaryl can contain one or multiple heteroatoms, for example, one to four heteroatoms, such as one or two heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, pyrimidine, and the like.

In certain aspects, the present disclosure relates to a diazirine precursor mass tag compound represented by structural formula (I)

(I)

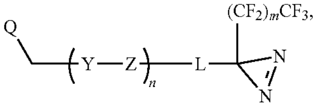

wherein, independently for each occurrence,

Q is —$NR^6R^7$, —$(NR^6R^7R^8)^+X^-$, —$(PR^6R^7R^8)^+X^-$, pyridyl, or

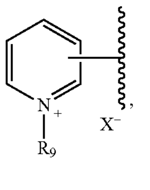

X is Hal, $NO_3$, $OC(O)CH_3$, $OC(O)C(CH_3)_3$, $OC(O)CF_3$, $HCO_3$, $AsO_2$, $H_2AsO_4$, $ASF_6$, $SO_3(C_4F_9)$, $SO_3(C_6F_{13})$, $SO_3C_8F_{17}$, $ClO_4$, CN, $BF_4$, $SnCl_3$, $CF_3SO_3$, or $C_6F_5O$;

$R^6$, $R^7$, $R^8$ is each independently $C_{1-6}$ alkyl or $C_{6-10}$ aryl;

$R^9$ is $C_{1-3}$ alkyl;

Y is $C_{6-10}$ aryl or 5-membered to 9-membered heteroaryl;

Z is —$(CH_2)_lA(CH_2)_k$—;

L is —$(CH_2)_lA(CH_2)_k$— or absent;

A is O, S, or NH;

l is 0 to 2;

k is 0 to 2;

m is 0 to 10; and n is 1 to 3.

In some embodiments, Q is —$(NR^6R^7R^8)^+X^-$ or —$NR^6R^7$. In some embodiments, Q is —$(NR^6R^7R^8)^+X^-$. In some embodiments, Q is —$NR^6R^7$. In some embodiments, Q is —$(PR^6R^7R^8)^+X^-$, pyridyl, or

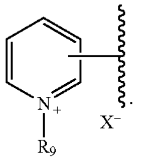

In some embodiments, pyridyl or

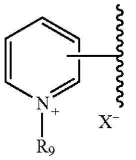

is substituted with one to two groups selected from $C_{1-3}$ alkyl and $NH_2$, or a combination thereof. In some embodiments, Q is —$(PR^6R^7R^8)^+X^-$.

In some embodiments, $R^6$, $R^7$, and $R^8$, if present, is each independently $C_{1-3}$ alkyl. In some embodiments, $R^6$, $R^7$, and $R^8$, if present, is each $C_2$ alkyl.

In some embodiments, X is Hal or $OC(O)CH_3$. In some embodiments, X is Hal. In some embodiments, X is F. In some embodiments, X is Cl. In some embodiments, X is Br. In some embodiments, X is $OC(O)CH_3$.

In some embodiments, Y is $C_{6-10}$ aryl. In some embodiments, Y is phenyl. In some embodiments, Y is 5-membered to 9-membered heteroaryl.

In some embodiments, one or more A is O. In some embodiments, one or more A is NH. In some embodiments, n is 3, at least one A is O, and at least one A is NH.

In some embodiments, L is —$(CH_2)_lA(CH_2)_k$—. In some embodiments, L absent.

In some embodiments, l is 0. In some embodiments, l is 1. In some embodiments, l is 2.

In some embodiments, k is 0. In some embodiments, k is 1. In some embodiments, k is 2.

In some embodiments, m is 0. In some embodiments, m is 1 to 3. In some embodiments, m is 1 to 3. In some embodiments, m is 1, 2, 3, 4, 5, 6, 7, 8, 9, or 10.

In some embodiments, the compound of formula (I) is selected from

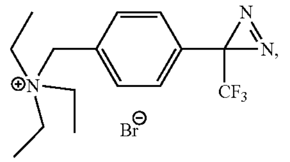

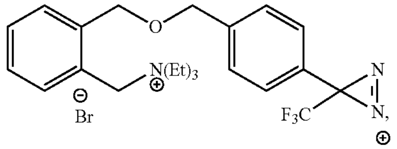

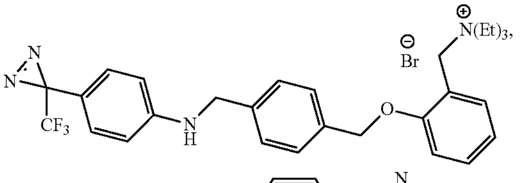

and

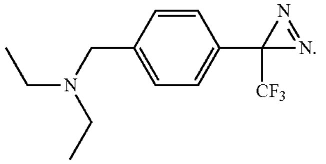

In certain aspects, the present disclosure relates to a method for detecting one or more analytes in a sample, comprising:

a) combining the sample and a reagent mixture, wherein the reagent mixture comprises a diazirine precursor mass tag reagent, and wherein the diazirine precursor mass tag reagent is a compound of formula (I), thereby generating an analyte mixture;

b) exposing the analyte mixture to a source of energy, thereby providing derivatized analyte mixture; and c) analyzing the one or more derivatized analytes, thereby detecting the one or more analytes.

In some embodiments, the sample further comprises a first solvent. In some embodiments, the first solvent is selected from the group consisting of water, a nitrile, dichloromethane, an alcohol, an ester, an ether, a hydrocarbon, a polyhalogenated hydrocarbon, and a combination thereof.

In some embodiments, the first solvent is selected from the group consisting of water, acetonitrile, dichloromethane, an alcohol, an ester, an ether, a hydrocarbon, a polyhalogenated hydrocarbon, an ionic liquid, a liquid containing micelles, and a combination thereof. In some embodiments, the first solvent is selected from the group consisting of an alcohol such as methanol; an ester such as ethyl acetate; an ether such as diethyl ether or t-butylmethyl ether; a hydrocarbon such as octane or toluene; a polyhalogenated compound such hexafluorobenzene, octafluorotoluene, dichloromethane, or trifluoromethyl trifluoroacetate; an ionic liquid; a liquid containing micelles; or a combination thereof.

In some embodiments, the first solvent is selected from the group consisting of water, a nitrile such as acetonitrile, an alcohol such as methanol or t-butanol; an ester such as ethyl acetate; an ether such as diethyl ether or t-butylmethyl ether; a hydrocarbon such as octane or toluene; a polyhalogenated compound such as hexafluorobenzene, octafluorotoluene, dichloromethane, or trifluoromethyl trifluoroacetate; an ionic liquid; a liquid containing micelles; or a combination thereof.

In some embodiments, the sample is a gaseous sample.

In some embodiments, the reagent mixture comprises a second solvent. In some embodiments, the second solvent is selected from any of the groups defined above for the first solvent.

In some embodiments, the second solvent is selected from the group consisting of water, acetonitrile, dichloromethane, an alcohol, an ester, an ether, a hydrocarbon, a polyhalogenated hydrocarbon, and a combination thereof. In some embodiments, the second solvent is selected from the group consisting of water, acetonitrile, dichloromethane, an alcohol, an ester, an ether, a hydrocarbon, a polyhalogenated hydrocarbon, an ionic liquid, a liquid containing micelles, and a combination thereof. In some embodiments, the second solvent is selected from the group consisting of water, acetonitrile, an alcohol such as methanol; an ester such as ethyl acetate; an ether such as diethyl ether or t-butylmethyl ether; a hydrocarbon such as octane or toluene; a polyhalogenated compound such hexafluorobenzene, octafluorotoluene, dichloromethane, or trifluoromethyl trifluoroacetate; an ionic liquid; a liquid containing micelles; or a combination thereof.

In some embodiments, the reagent mixture comprises a third solvent. In some embodiments, the third solvent is selected from the group consisting of water, acetonitrile, dichloromethane, chloroform, carbon tetrachloride, tetrahydrofuran, 2-methyltetrahydrofuran, DMF, dimethylsulfoxide, NMP, acetone, diphenyl oxide, methyl isobutyl ketone, halogenated esters such as trifluoromethyl trifluoroacetate or pentafluoroethyl trifluoroacetate, hexaflurobenzene, an ionic liquid, a liquid containing micelles, and a combination thereof.

In some embodiments, the polyhalogenated hydrocarbon is hexafluorobenzene or octafluorotoluene.

In some embodiments, the reagent mixture comprises a solid support. In some embodiments, the carbene reagent is deposited on the solid support.

In some embodiments, the source of energy is selected from the group consisting of UV photons, LED photons, UV LED photons, heat, laser photons, electrons, photons from fluorescence energy transfer, plasma, a metastable compound, an energy-releasing molecule, a vibrationally-activated molecule, and a combination thereof. In some embodiments, the energy-releasing molecule is selected from the group consisting of ozone, an ozonide, and a peroxide. In some embodiments, the source of energy is selected the group consisting of from UV photons, LED photons, and UV LED photons, and a combination thereof. In some embodiments, the source of energy is UV LED photons. In some embodiments, the source of energy is heat.

In some embodiments, the derivatized analyte mixture further comprises one or more calibration standard. In some embodiments, the one or more calibration standard is selected from the group consisting of $D_2O$, butanol, ethylene glycol, cyclooctane, naphthalene, $CD_3CD_2OH$, and perfluorobutanol.

In some embodiments, the method further comprises treating the derivatized analyte mixture with a carbene-reactive scavenger agent before step c), thereby generating a scavenged carbene reagent. In some embodiments, the scavenger agent is selected from the group consisting of silica, agarose, chitin, dextrin, pectin, polyethylene glycol, polyacrylamide, ethylenediamine-substituted polyacrylamide, cellulose, paper, nylon, albumin, a dendrimer, polymethacrylate, polyvinylchloride, polyvinylpyrollidone, cellulose acetate, a polypeptide, a carbohydrate, a diamine, collagen, a triglyceride, lecithin, a dihydrazide, and glucocerebroside. In some embodiments, the method further comprises removing the scavenged carbene reagent from the derivatized analyte mixture before step c). In some embodiments, the scavenged carbene reagent is removed from the derivatized analyte mixture by a purification method selected from the group consisting of filtration, centrifugation, magnetic attraction, precipitation, adsorption, absorption, liquid or solid phase extraction, liquid chromatography, and size exclusion chromatography.

In some embodiments, analyzing the one or more derivatized analytes comprises analyzing the derivatized analyte mixture by an analytical method selected from the group consisting of ion mobility mass spectrometry, liquid chromatography-electrospray ionization mass spectrometry, infusion-electrospray ionization mass spectrometry, and matrix-assisted laser desorption ionization mass spectrometry. In some embodiments, the analytical method is ion mobility mass spectrometry or matrix-assisted laser desorption ionization mass spectrometry. In some embodiments, the analytical method is matrix-assisted laser desorption ionization mass spectrometry.

In some embodiments the present disclosure relates to a compound having an $R_1$-aryl$_1$-$CHR_2$—$NR_3R_4R_5$ (RACN) moiety and a single polyfluoroalkyldiazirine (PFAD) group, wherein $R_1$ is H, $XCH_3$, $XCH_2CH_3$, $CH_2XCH_3$, or $CH_2XCH_2CH_3$ with X═O or S, or $R_1$ is a group that connects to a PFAD group; $R_2$ is H or a group that connects to a PFAD group; $R_3$ is H or an alkyl or aryl group having 6 or fewer carbon atoms; and each of $R_4$ and $R_5$ is an alkyl or aryl group having 6 or fewer carbon atoms.

In some embodiments, $R_1$ is ortho to $CHR_2$—$NR_3R_4R_5$.

In some embodiments, the PFAD group is directly attached to aryl$_1$.

In some embodiments, aryl$_1$ is phenyl.

In some embodiments, aryl$_1$ is pyridine or pyrimidine.

In some embodiments, the PFAD group is $CF_3$, $C_2F_5$, $C_3F_7$, or $C_4F_9$

In some embodiments, compound is CAX-DZ, CAX-DZ-2, CAX-DZ-3, or DEA-DZ.

In some embodiments the present disclosure relates to a method in which one or more organic or organometallic analyte compounds in a sample are detected by a process comprising the following sequence of steps: (1) combining the sample with a reagent compound comprising a diazirine group and a secondary, tertiary, or quaternary amine group in the presence or absence of solvent, giving a combined sample; (2) subjecting the combined sample in a vessel or tube or gas phase to sufficient energy to release a molecule of nitrogen from the diazirine group, yielding a reactive intermediate having a carbene moiety and a secondary, tertiary or quaternary amine group, which reactive intermediate in turn reacts covalently with one or more of the said analyte compounds to form one or more corresponding products, and then, optionally, adding a carbene-reactive substance as a scavenger and continuing the energy exposure; and (3) detecting one or more of the said products or a fragment thereof in a system comprising a mass spectrometer or an ion mobility spectrometer.

In some embodiments, each of $R_3$, $R^4$ and $R_5$ is alkyl or aryl, creating a positive charge, where the counterion for this positive charge is a bromide, chloride, fluoride, nitrate, acetate, trifluoroacetate, pivalate, bicarbonate, arsenite, dihydrogenarsonate, hexafluoroarsenate, perfluorobutane sulfonate, perfluorohexane sulfonate, perfluorooctane sulfonate, perchlorate, cyanide, tetrafluoroborate, trichlorostannate, trifluorosulfonate, or pentafluorophenolate.

In some embodiments, each of $R_3$, $R^4$ and $R_5$ is alkyl or aryl, creating a positive charge, where the counterion for this positive charge is a bromide, chloride, fluoride, nitrate, acetate, trifluoroacetate, perfluorobutane sulfonate, perfluorohexane sulfonate, pentafluorophenolate, bicarbonate, or arsonate.

In some embodiments, the solvent, when present, comprises a polyhalogenated compound or acetonitrile.

In some embodiments, halogen is fluorine.

In some embodiments, the polyhalogenated compound comprises hexafluorobenzene or octafluorotoluene.

In some embodiments, the reagent compound is a compound having an $R_1$—aryl$_1$-$CHR_2$—$NR_3R_4R_5$ (RACN) moiety and a single polyfluoroalkyldiazirine (PFAD) group, wherein $R_1$ is H, $XCH_3$, $XCH_2CH_3$, $CH_2XCH_3$, or $CH_2XCH_2CH_3$ with X═O or S, or $R_1$ is a group that connects to a PFAD group; $R_2$ is H or a group that connects to a PFAD group; $R_3$ is H or an alkyl or aryl group having 6 or fewer carbon atoms; and each of $R^4$ and $R_5$ is an alkyl or aryl group having 6 or fewer carbon atoms.

In some embodiments, the vessel or tube comprises metal or consists of a glass or plastic container enshrouded in metal.

In some embodiments, in which the energy is provided by one or more or the following: UV photons, laser photons, LED photons, heat, electrons, photons from fluorescence energy transfer, metastable compounds, plasma, ozone or ozonide.

In some embodiments, which a product is detected by ion mobility spectrometry, liquid chromatography-electrospray ionization mass spectrometry, infusion-electrospray ionization mass spectrometery, or matrix-assisted laser desorption ionization mass spectrometry.

In some embodiments, the scavenger is a polymer or particle.

In some embodiments, the secondary amine is a picolinoyl group.

In some embodiments, the tertiary amine is pyridinoyl or 3-aminopyridyl group.

In some embodiments, the quaternary amine is a pyridinium ion.

EXAMPLES

Abbreviations used in the following examples and elsewhere herein are:

ACN acetonitrile
CHCA alpha-cyano-4-carboxycinnamic acid
DEA diethylamine
DMSO dimethyl sulfoxide
EA ethyl acetate
ESI electrospray ionization
GC-MS gas chromatography-mass spectrometry
h hour(s)
HPLC high-performance liquid chromatography
LC-MS liquid chromatography-mass spectrometry
MALDI-TOF MS matrix-assisted desorption-ionization time-of-flight mass spectrometry
MALDI-TOF-TOF-MS MALDI-TOF/TOF tandem mass spectrometry
min minutes
R.T. room temperature
TEA trimethylamine
NMP N-methylpyrollidone
DMF N,N-Dimethylformamide Materials Compounds 1a and 2a were purchased from TCI America, and the Oasis™ HLB cartridges (6cc) were purchased from Waters, USA. Other reagents, chemicals, and solvents including acetonitrile (ACN) were purchased from Sigma Aldrich, USA. The UV light came from a UV 1800 Stratalinker from Stratagene or light-emitting diode (LED, model number XLTO18UVC/345). CHCA matrix contained alpha-cyano-4-carboxycinnamic acid, 5 mg/mL in 50% ACN.

Example 1

Synthesis of Diazirine Compounds

Note: Procedures such as reaction setup, synthesis, reaction workup, concentration, evaporation, and purification of diazirine-containing reaction mixtures were performed in the dark or with minimal light exposure.

Compound CAX-DZ

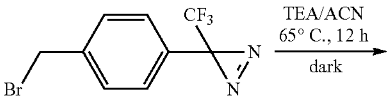

1a

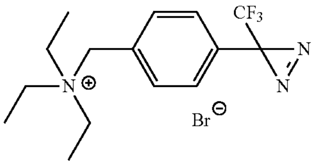

CAX-DZ

Compound 1a (10 mg, 0.0358 mmol) was placed in a 2 mL amber glass vial and dissolved in 400 μL of acetonitrile. Triethylamine (20 μL) was added to the mixture, the vial was closed and heated at 65° C. for 12 h in dark. The contents were allowed to cool to room temperature, and all volatiles were removed using vacuum. The residue was dissolved in 0.5 mL of ACN and loaded onto the OASIS™ HLB cartridge, which was allowed to dry for one hour. The cartridge was washed and eluted by applying the following sequence: 2 ml of 5% ACN in water; 3 mL of 20% ACN; 4 mL of 50% ACN; and 1 mL of 95% ACN. The last two fractions were combined and the volatiles were removed under vacuum to give compound CAX-DZ. The compound was stored in the dark at 4° C., and aliquots were taken and weighed to prepare stock solutions.

Compound CAX-DZ-2

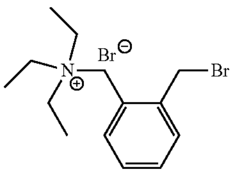

CAX-B

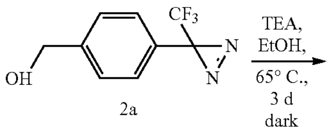

-continued

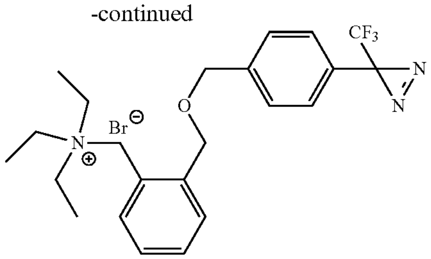

CAX-DZ-2

In a 2 mL amber glass vial CAX-B (12 mg, 0.0328 mmol) and compound 2a (7 mg, 0.0323 mmol) were dissolved in 400 μL of ethanol. Triethylamine (20 μL) was added to the mixture, the vial was closed and heated at 65° C. for 3 days in dark. The contents were allowed to cool to room temperature, and all volatiles were removed using vacuum. The residue was dissolved in 0.5 mL of ACN and loaded onto the OASIS™ HLB cartridge, which was allowed to dry for one hour. The cartridge was washed and eluted by applying the following sequence: 1 mL of 5% ACN, 2 mL of 25%, 2 mL of 35%, 2 mL of 50%, and 1 mL of 95%. The last two fractions were combined and the volatiles were removed under vacuum to give compound CAX-DZ-2. The compound was stored in the dark at 4° C., and aliquots were taken and weighed to prepare stock solutions.

Compound CAX-DZ-3 (compound 4c)

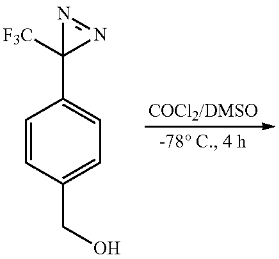

4a
Commercially available

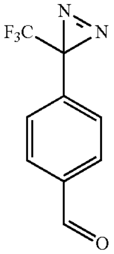

4b

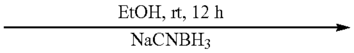

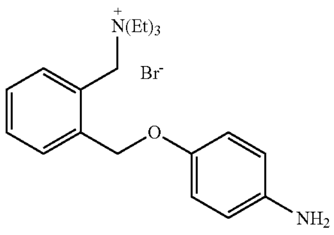

CAX-A

-continued

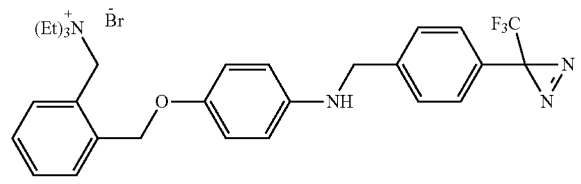

CAX-DZ-3
4c

Synthesis of Aldehyde 4b

This compound was synthesized as described (Stolze, S. C. et al., Photo-crosslinking of clinically relevant kinases using H89-derived photo-affinity probes, Journal of the Royal Society of Chemistry, Mol. BioSyst. [2016] 1809-1817).

In a 20 mL vial, DMSO (322 μL, 4.54 mmol) was cooled to −78° C. and oxalyl chloride (206 μL, 2.40 mmol) was added dropwise. The reaction mixture was stirred for 30 min at −78° C. A solution of alcohol 2a (40 mg, 0.185 mmol) in dichloromethane (4 mL) was added slowly. The reaction mixture was stirred for 1 h at −78° C. TEA (1.26 mL, 9.08 mmol) was slowly added at −78° C. The reaction mixture was allowed to warm to 0° C. and was subsequently stirred for 3 h. This reaction mixture was added to a cold aqueous solution of 20% $KH_2PO_4$ (5 mL) and cold $H_2O$ (20 mL), and the resulting mixture was stirred for 15 min at RT. The mixture was diluted with ether (20 mL), and the layers were separated. The organic layer was washed with a cold aqueous solution of 10% $KH_2PO_4$ (3×10 mL) and brine, dried over $MgSO_4$, filtered and evaporated in vacuum to give a residue which was purified by column chromatography (#400 silica, 2.5×18 cm), and eluted progressively with 800 mL volumes each of 1%, 2%, 3%, 4%, and 5% ethyl acetate in hexane. The product was obtained as a pale yellow oil of aldehyde 4b (yield: 31 mg, 0.145 mmol, 78%), and its structure was confirmed by mass spectrometry.

Synthesis of Diazirine 4c (CAX-DZ-3)

In a 2 mL amber glass vial CAX-A (60 mg, 0.152 mmol) and compound 4b (30 mg (0.14 mmol) were dissolved in 600 μL of ethanol. The vial was closed and heated at 65° C. for 8 h in the dark. The contents were allowed to cool to room temperature. Sodium cyanoborohydride (30 mg, 0.477 mM) was added to reaction mixture portion-wise, the vial was closed and the reaction mixture was allowed to stir for 30 min at room temperature. All volatiles were removed under vacuum. The residue was dissolved in 0.5 mL of ACN and loaded onto the OASIS™ HLB cartridge, which was allowed to dry for one hour. The cartridge was washed and eluted by applying the following sequence: 1 ml of 5% ACN, 5 mL of 25% ACN, 3 mL of 50%, and 1 mL of 95%. The last two fractions were combined and the volatiles were removed under vacuum to give compound CAX-DZ-3. The compound was stored in the dark at 4° C., and aliquots were taken and weighed to prepare stock solutions.

Compound DEA-DZ

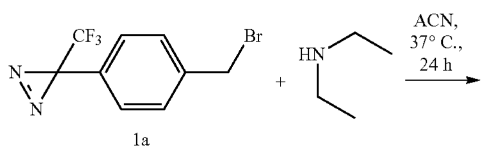

1a

-continued

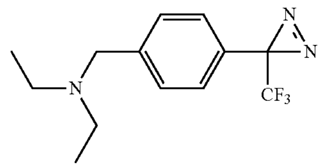

DEA-DZ

In a 2 mL amber glass vial compound 1a (10 mg, 0.0358 mm) was dissolved in 300 μL of acetonitrile. To this vial was added 20 μL of diethylamine, the vial was closed and heated at 37° C. for 24 h in dark. The contents were allowed to cool to room temperature, and all volatiles were removed under vacuum to give DEA-DZ. DEA-DZ was stored in dark at 4° C., and aliquots were taken and weighed to prepare stock solutions.

Acetate Salt of CAX-DZ

Aqueous solution of CAX-DZ (2 mg/mL) was added to 1 mL of silver acetate solution (3 mg/mL in water). The solution was vortexed for 1 min and centrifuged for 10 min at 13.5 g. The supernatant was transferred to a new vial, and contents were evaporated to dryness under vacuum. The dried residue was stored in amber vials. Other counterions such as fluoride, nitrate, trifluoroacetate, chloride, perfluorobutane sulfonate, perfluorohexane sulfonate, pentafluorophenolate, bicarbonate, or arsonate can be substituted similarly or by ion exchange chromatography of the bromide.

Example 2

Synthesis of diazirene mass tag having a methoxy moiety ortho to a triethylaminomethylene moiety enabling anchimeric-assisted neutral loss of triethylamine under collision-induced dissociation conditions in a tandem mass spectrometer.

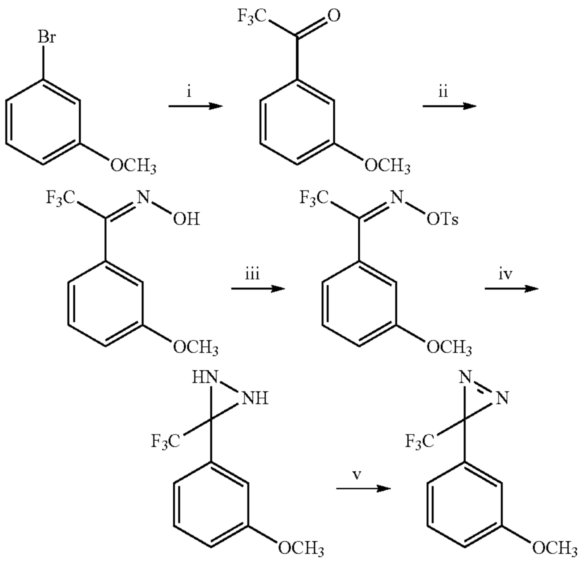

-continued

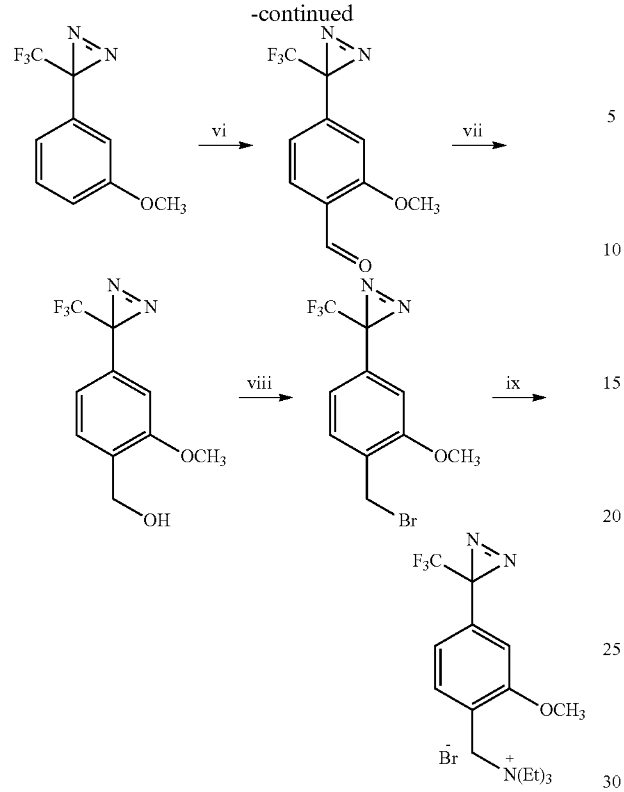

Reagents and conditions:
i) n-BuLi then $CF_3CO_2Me$;
ii) $NH_2OH{\bullet}HCl$, $C_5H_5N$;
iii) TsCl, $C_5H_5N$,
iv) Condensed $NH_3$;
v) $I_2$, $Et_3N$, MeOH;
vi) $TiCl_4$, $Cl_2CHOMe$, $CH_2Cl_2$,
vii) $NaBH_4$,
viii) $PPh_3$, $CBr_4$, $Et_2O$,
ix) $Et_3N$, AcN.

Example 3

Labeling and Detection of Opioids

Figure 5:
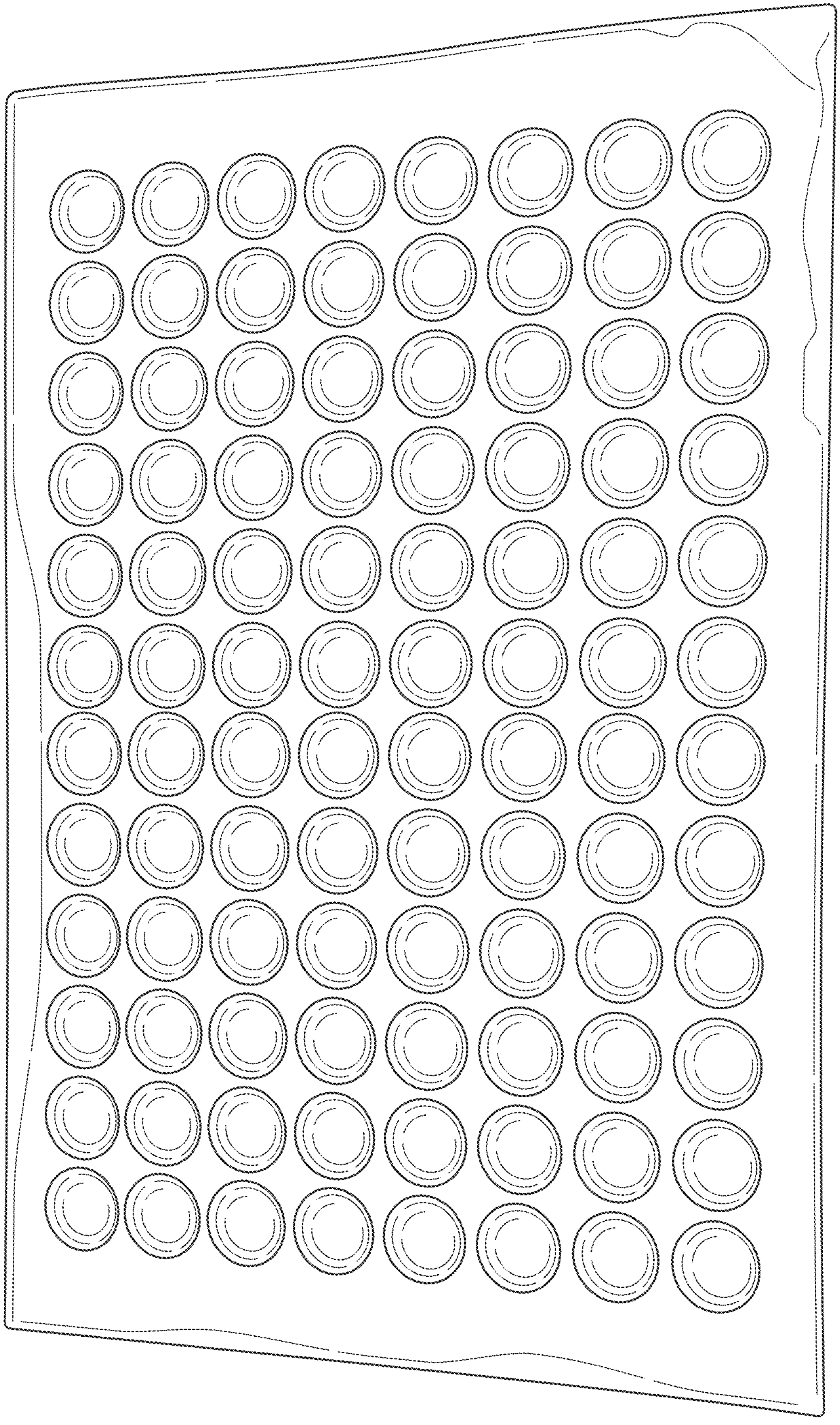
FIG. 5 shows a photograph of well impressions on an aluminum foil surface made by laying down a sheet of aluminum foil and making wells by pressing with a finger while wearing a glove.

An aluminum foil was wrapped around a 96 well plate and pressed gently on the wells with a glove covered finger to create concave well impressions on the foil surface. These impressions were used as a mini-wells for carrying out the reaction (see FIG. 5).

Figure 6:
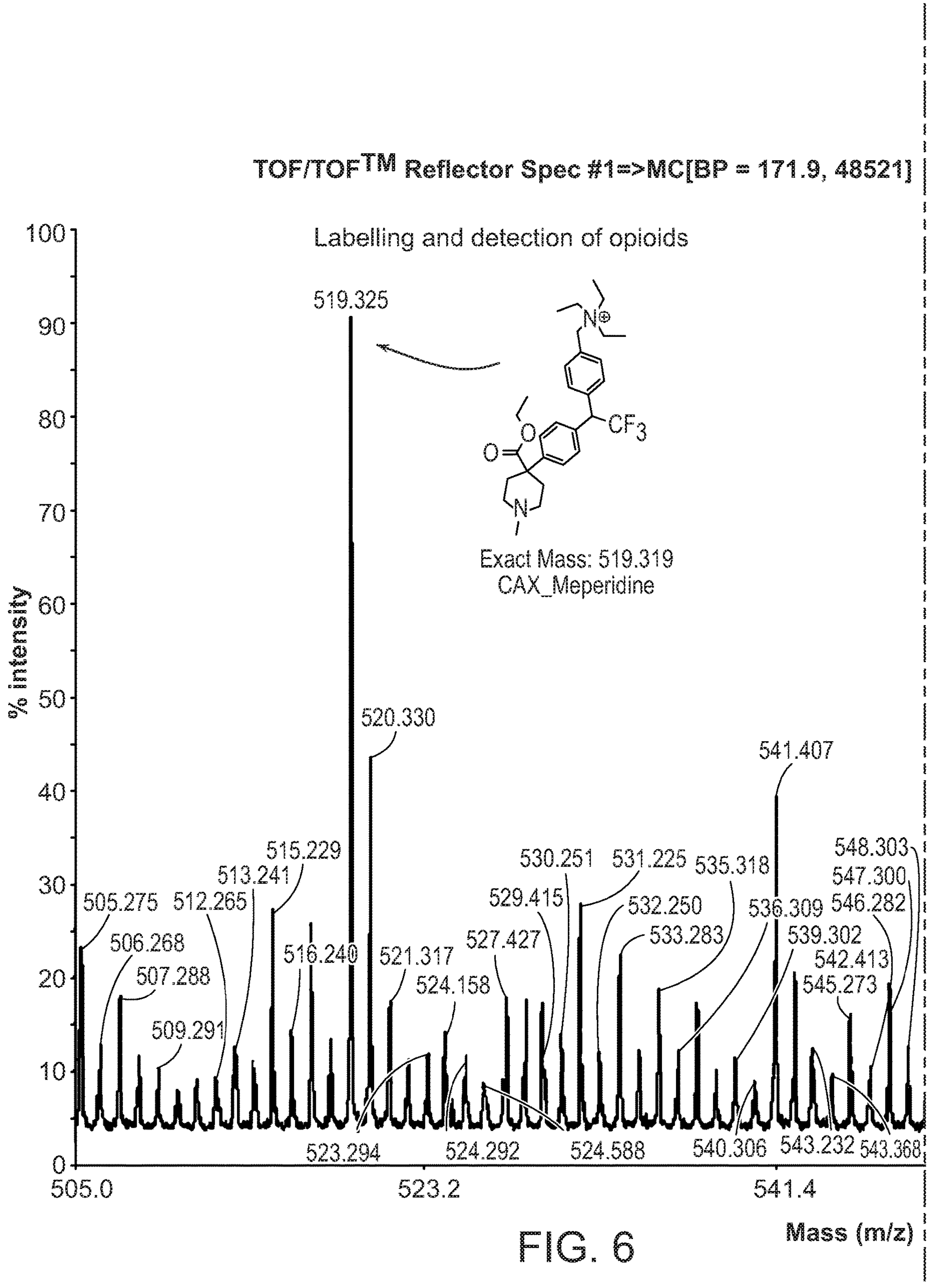
FIG. 6 shows a mass spectrum demonstrating CAX-DZ/UV/MALDI-TOF-MS detection of opioids
Figure 6:
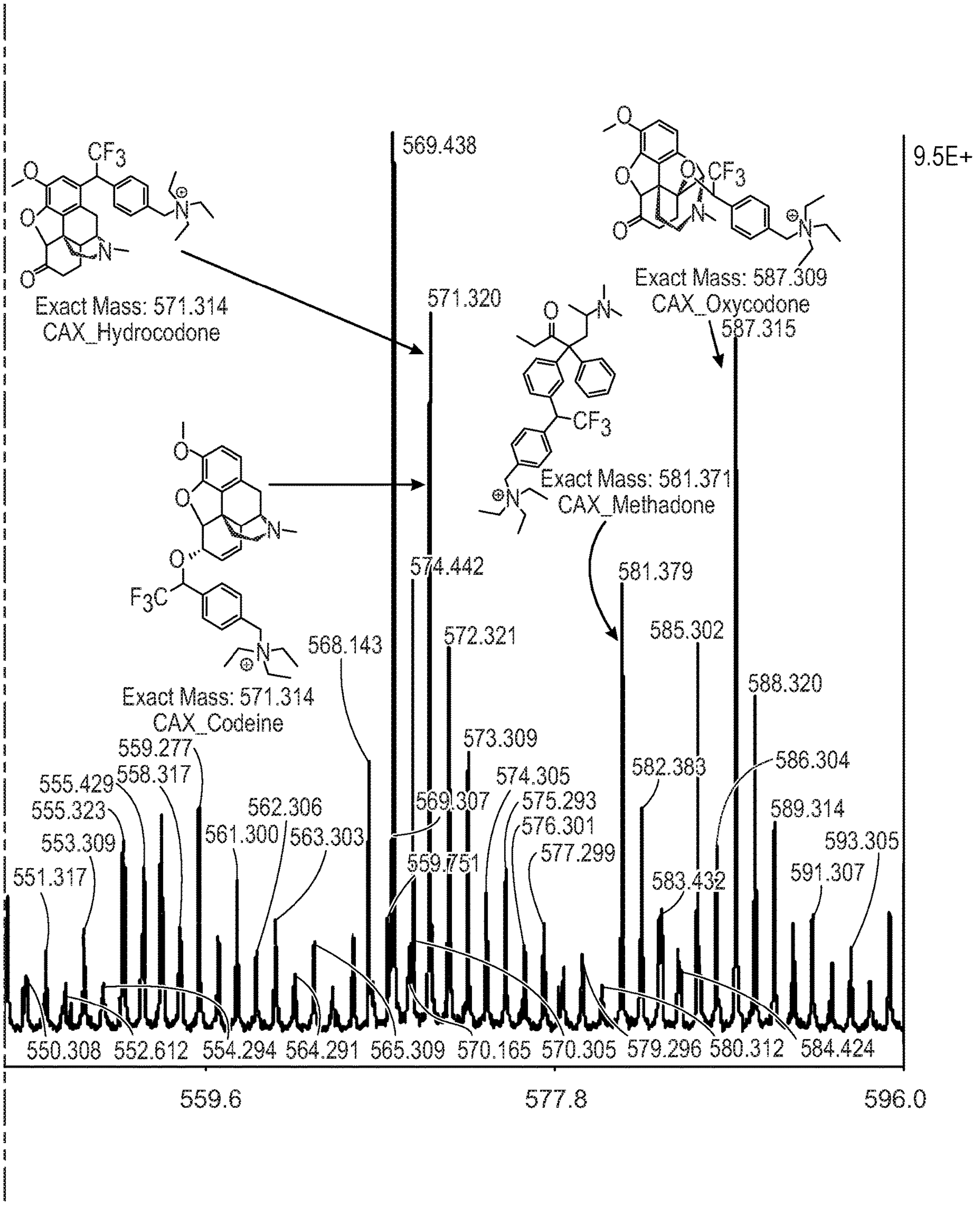

Onto a mini-well, 1 μL of Opiate multi-component mixture-5 solution (250 μg/mL) was applied and allowed to dry followed by addition of 5 μL of CAX-DZ reagent (100 μg/mL in ACN) and mixed using a pipette tip. This plate was then kept under UV light for 2 min. To the mini-well was added 10 μL of 50% ACN and contents were quantitatively transferred from each of the mini-wells to a separate vial containing 100 μL of CHCA matrix respectively. About 0.7 μL of this mixture was taken per spot on MALDI-TOF plate and analyzed using MALDI-TOF-TOF-MS. The results of the experiments are shown in FIG. 6.

Example 4

Labeling and Detection of Cannabinoids from the Crude Plant

Crude Plant:

Chronic 3.5 g (Hybrid) from Alternative Therapies Group, Salem, MA 01970). Extraction of the crude plant to give an extract: In a 20 mL scintillation vial 190 mg of the crude plant was suspended in 14 mL of the following solvent mixture: acetone: methanol (1:1). The vial was closed and vortexed for 5 min (30 s×10) to give a green solution. The contents were allowed to settle. One milliliter of the upper solvent layer was transferred in a 2 mL Eppendorf tube and concentrated under vacuum to about 100 μL.

Figure 7:
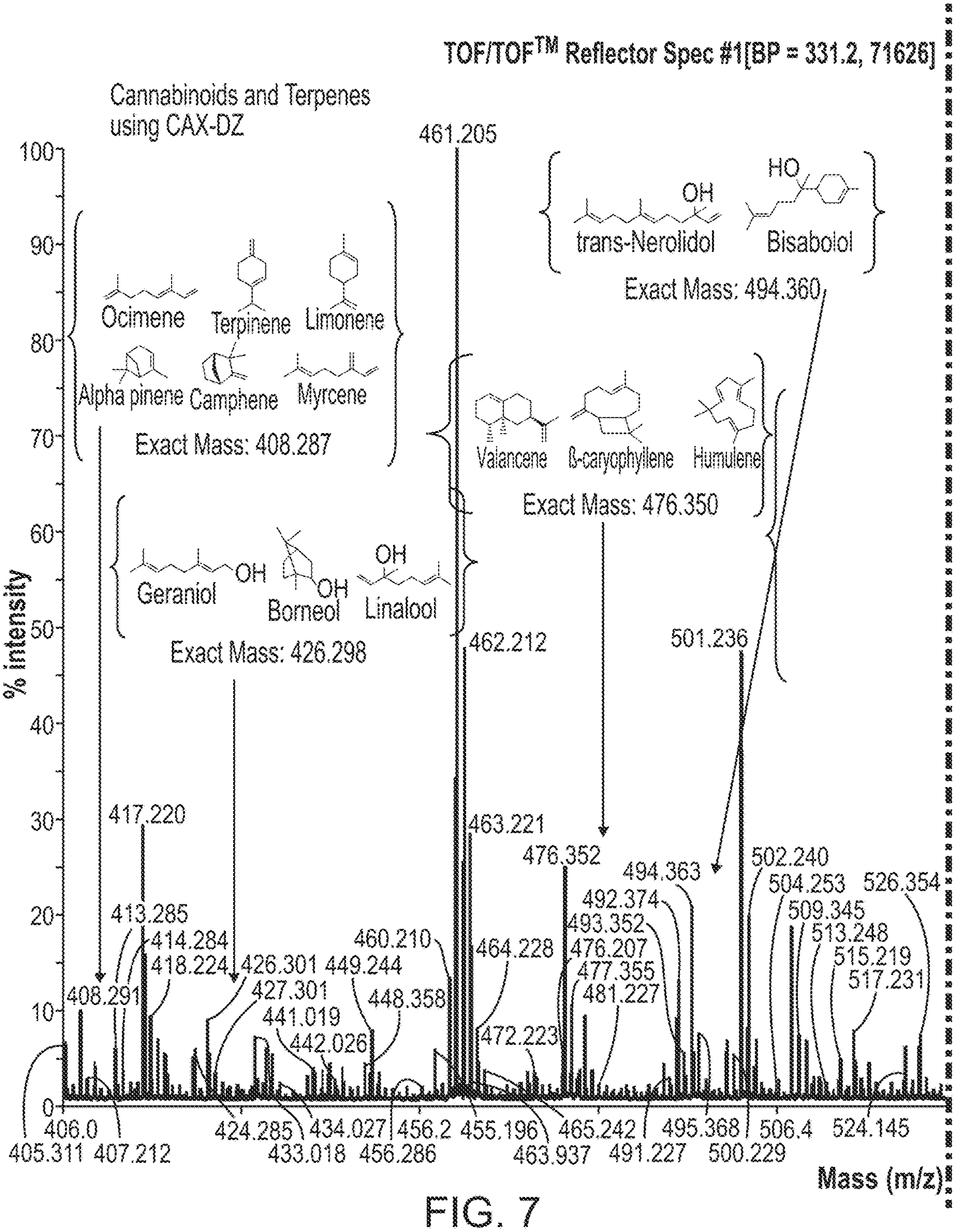
FIG. 7 shows a mass spectrum demonstrating CAX-DZ/UV/MALDI-TOF-MS detection of cannabinoids and terpenes from a crude cannabis plant.
Figure 7:
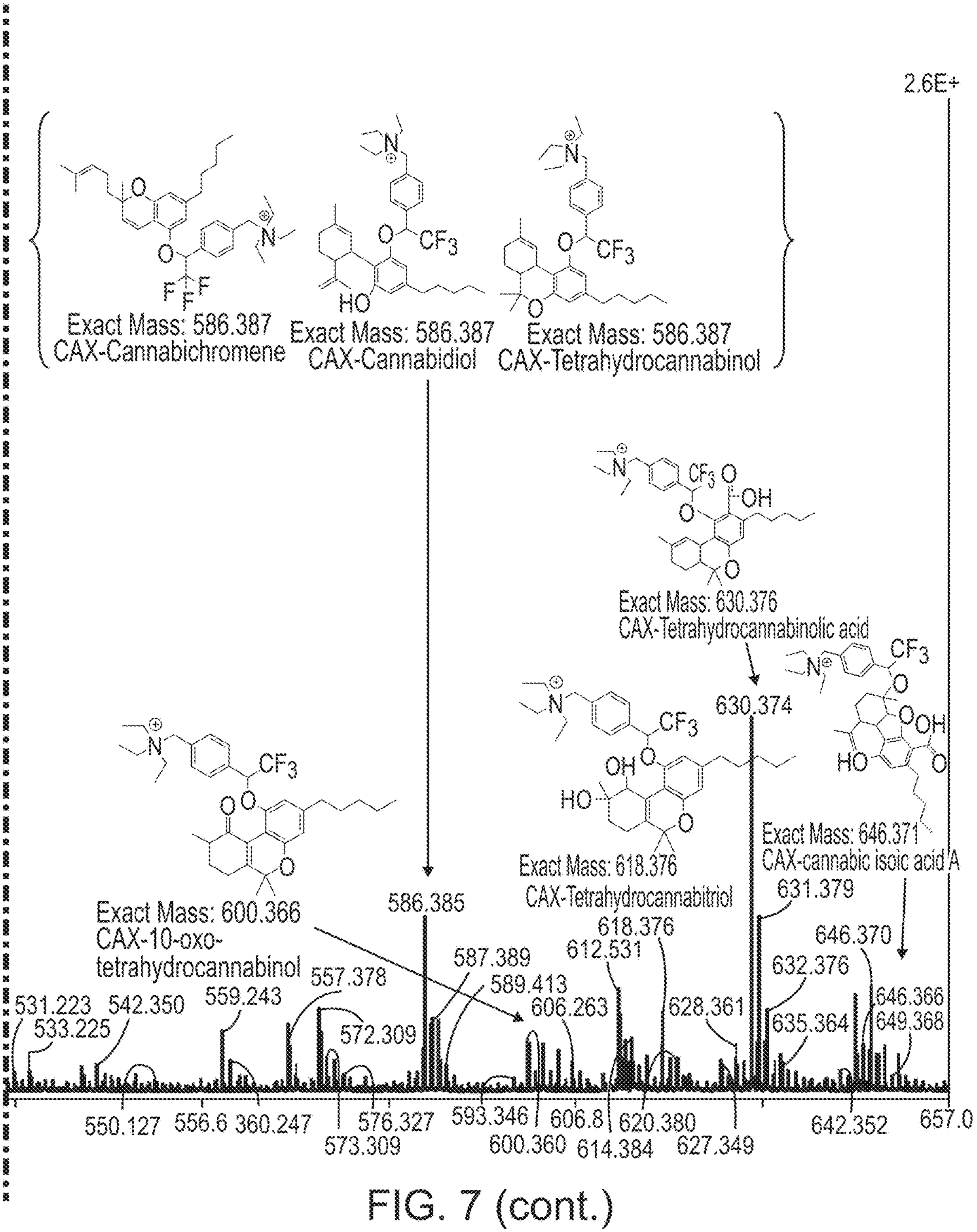

Labeling and Analysis:

Onto a mini-well, 5 μL of the crude extract solution was applied and allowed to dry followed by addition of 5 μL of CAX-DZ reagent (1 mg/mL) and mixed using a pipette tip. This plate was then kept under UV light for min, then taken out and reconstituted with 10 μL of acetonitrile. This plate was then kept again under UV light for 3 min. To this mini-well was added 10 μL of 50% ACN and all contents of the mini-well were transferred to a separate vial containing 100 μL of CHCA matrix. About 0.7 μL of this mixture was taken per spot onto a MALDI-TOF-MS plate and analyzed using MALDI-TOF-TOF-MS. The results of the experiments are shown in FIG. 7.

Example 5

Labeling and Detection of Poly Aromatic Hydrocarbons (PAH)

Figure 8:
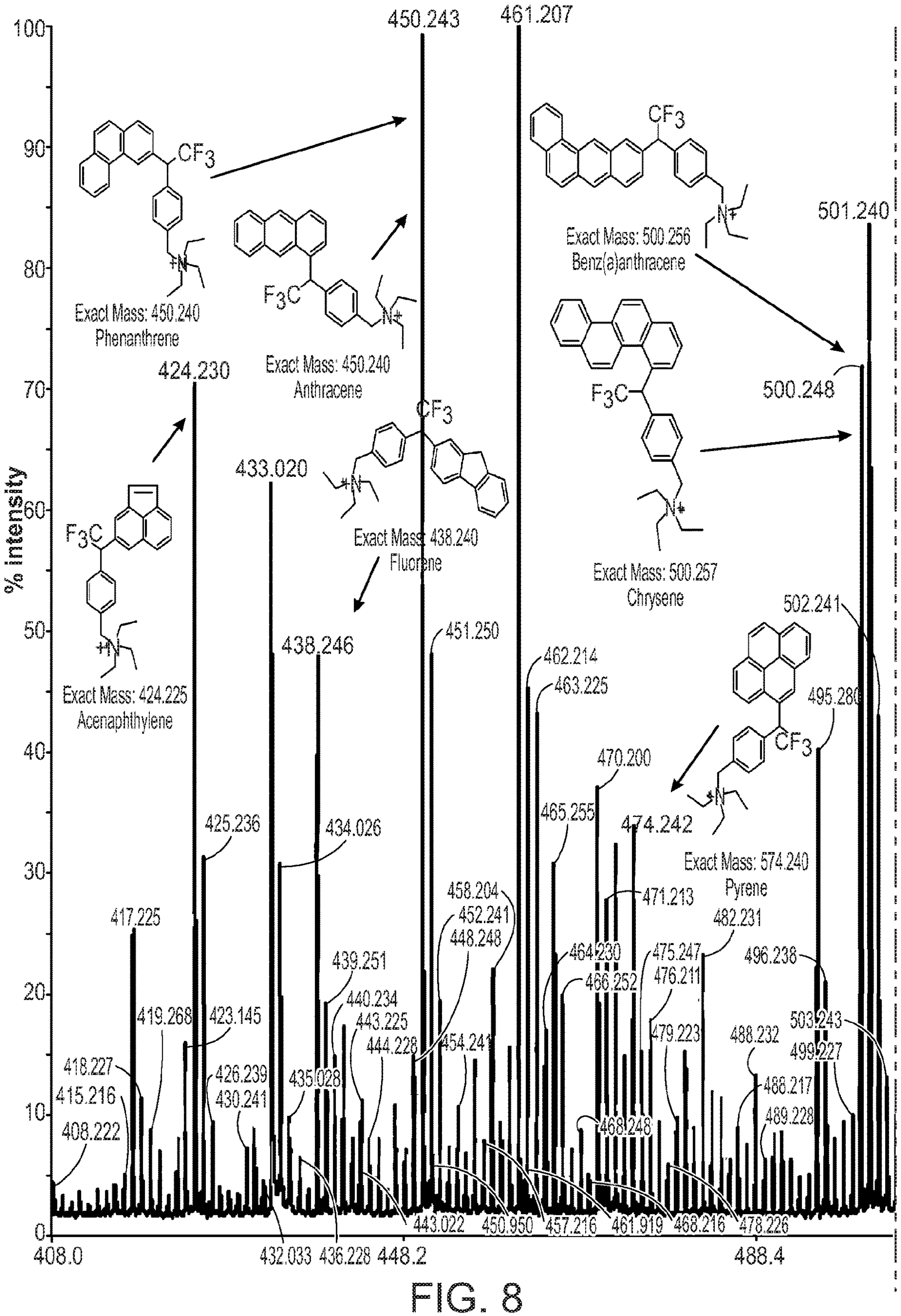
FIG. 8 shows a mass spectrum demonstrating CAX-DZ/UV/MALDI-TOF-MS detection of polyaromatic hydrocarbons.
Figure 8:
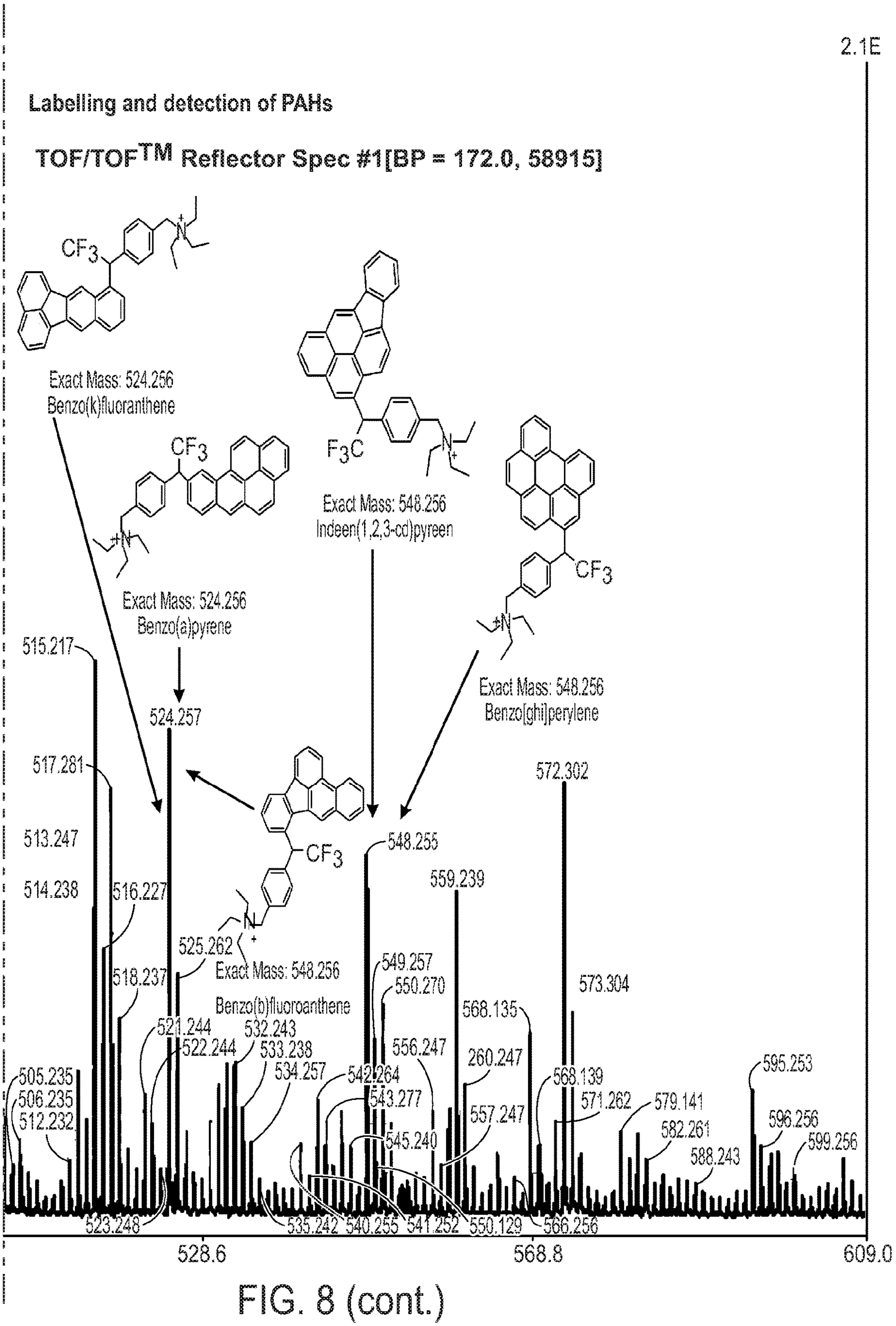

EPA 525 PAH Mix A: Certified reference material, 500 μg/mL each component in dichloromethane Onto a mini-well 1 μL of EPA 525 PAH Mix A (500 μg/mL) was applied and allowed to dry followed by addition of 5 μL of CAX-DZ reagent (1 mg/mL in ACN) and mixing using a pipette tip. The plate was then kept under UV light for 2 min. To this well was added 10 μL ACN, mixed well using a micropipette tip and kept under UV light for 2 min. To the mini-well was added 10 μL of 50% CAN, and the contents of the mini-well were transferred to a separate vial containing 100 μL of CHCA matrix. About 0.7 μL of this mixture was taken per spot on MALDI-TOF plate and analyzed using MALDI-TOF-TOF-MS. The results of the experiments are shown in FIG. 8.

Example 6

Analysis of Saliva Using CAX-DZ/LED/MALDI-MS

Figure 9:
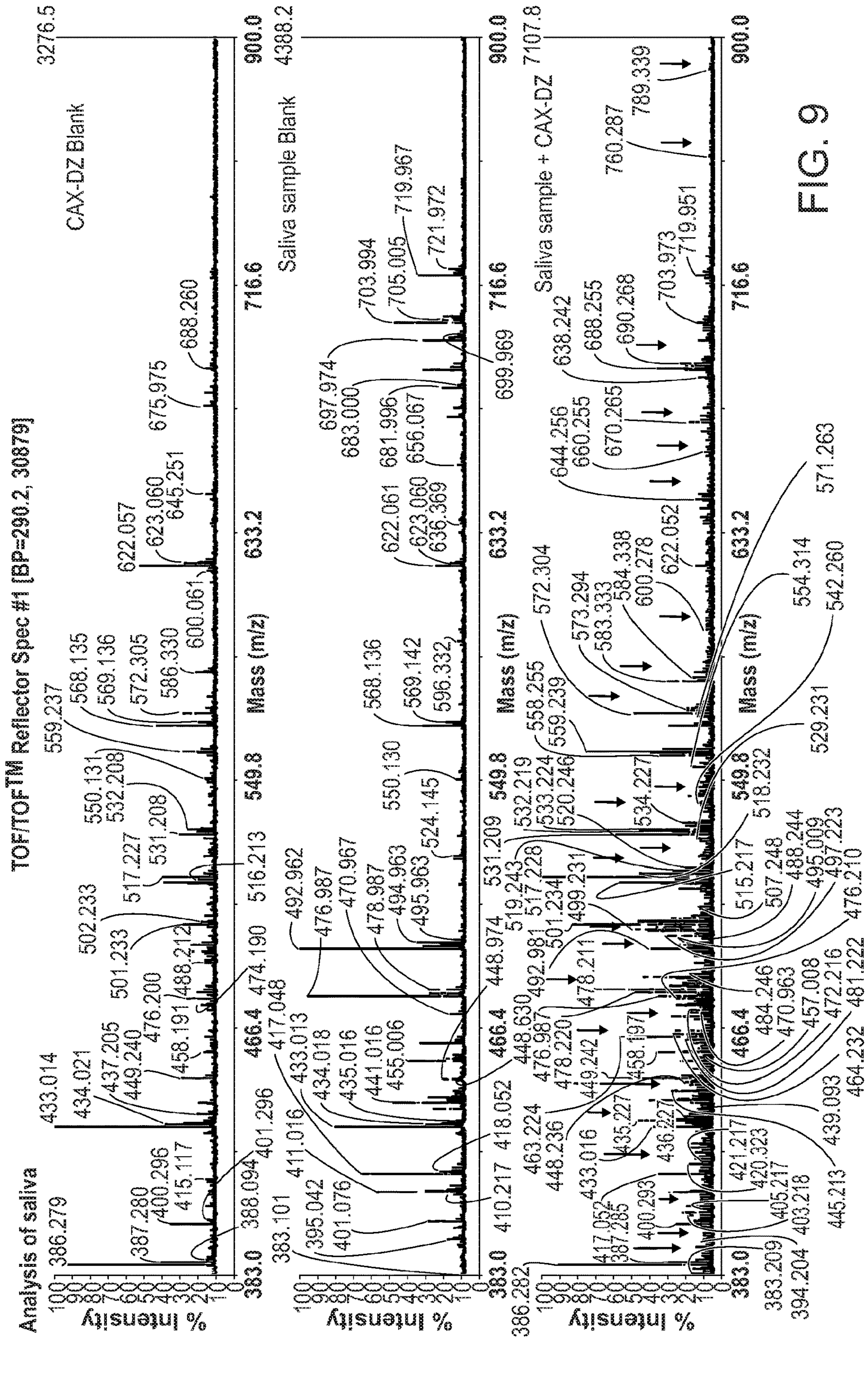
FIG. 9 shows mass spectra demonstrating CAX-DZ/UV/MALDI-TOF-MS detection of saliva metabolites.

Onto a mini-well 10 μL of saliva was taken and allowed to air dry, it was followed by addition of 5 μL of CAX-DZ reagent (1 mg/mL in ACN) and mixed using a pipette tip. This plate was then kept under UV light for 2 min. To this well was added with 10 μL ACN, mixed well using micropipette tip and kept under UV light for 2 min. To the mini-well was added 10 μL of 50% ACN and the contents of the mini-well were transferred to a separate vial containing 100 μL of CHCA matrix. About 0.7 μL of this mixture was taken per spot on MALDI-TOF plate and analyzed using MALDI-TOF-TOF-MS. The results of the experiments are shown in FIG. 9.

Example 6

Labeling and Analysis of a Raspberry Sample

About 1 g of raspberry was gently crushed in a 15 mL centrifuge tube using a micro spatula. To it was added 5 mL of extraction solvent (acetone: methanol, 1:1). The tube was sealed and vortexed for 5 min (30 s intervals) followed by centrifugation to separate the insoluble fraction. The supernatant was transferred to another tube and evaporated to dryness. The residue was dissolved in 2 mL of 70% acetonitrile and used for further analysis.

Figure 10:
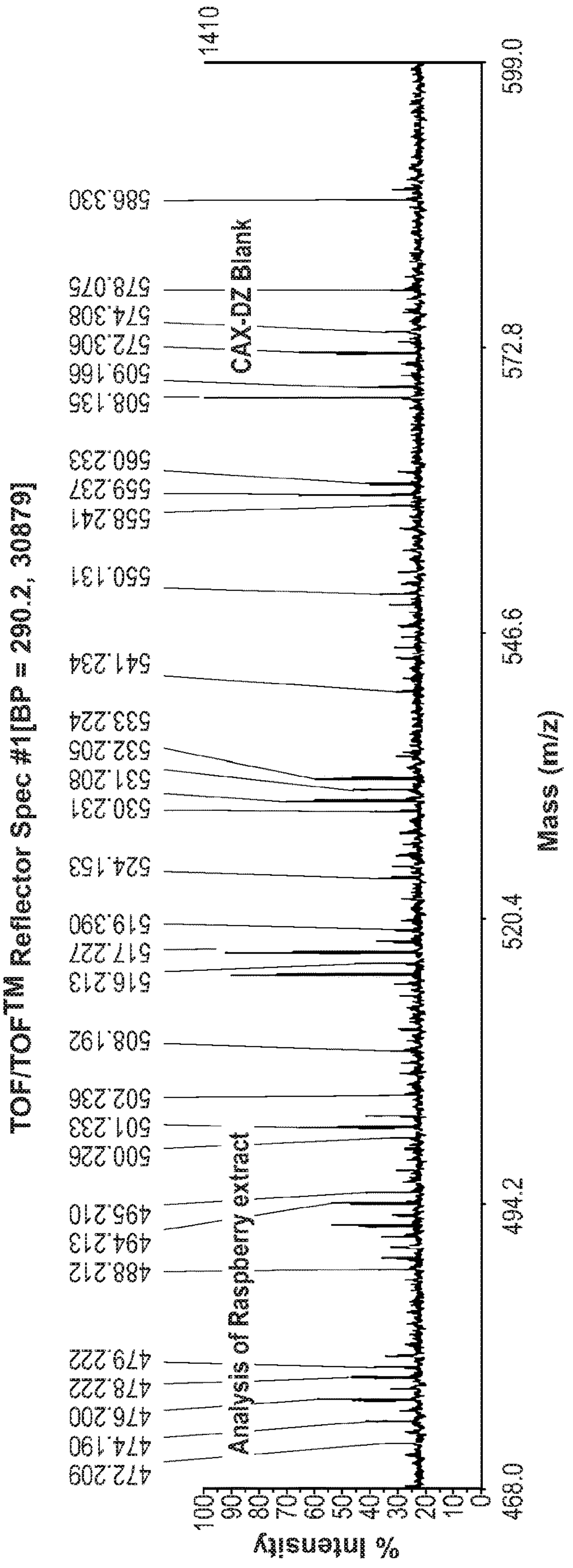
FIG. 10 shows mass spectra demonstrating CAX-DZ/UV/MALDI-TOF-MS detection of raspberry metabolites.
Figure 10:
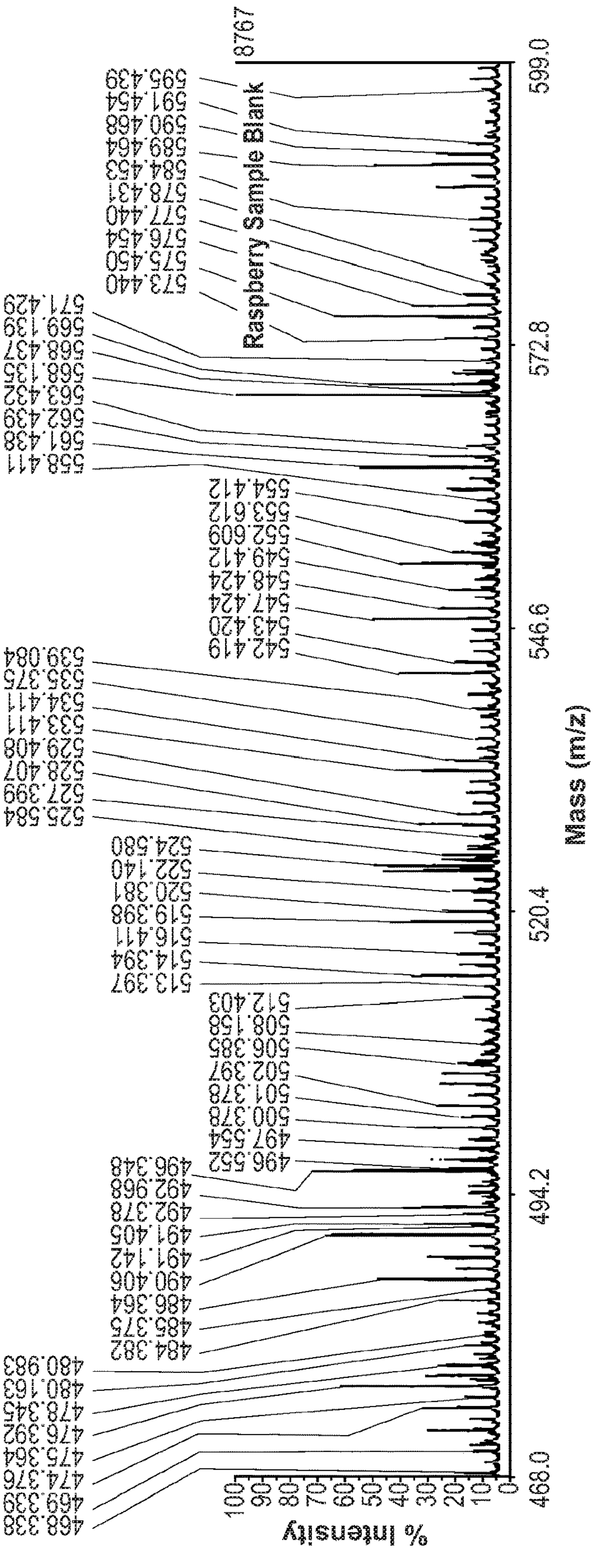
Figure 10:
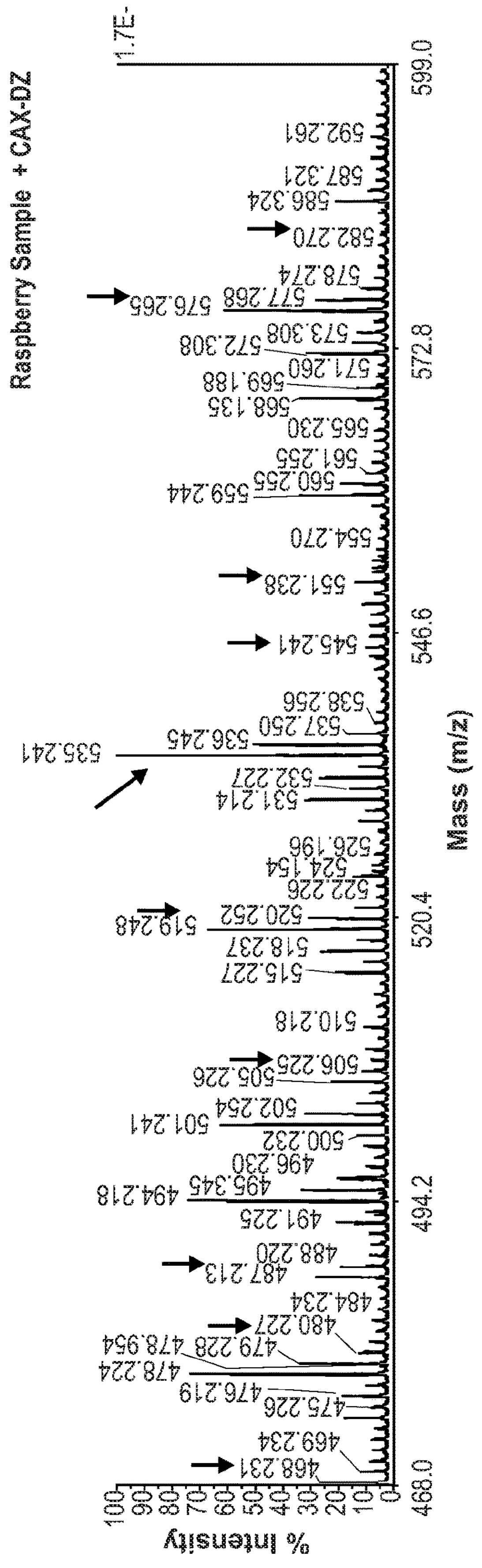

In a mini-well 10 μL of water and 5 μL of CAX-DZ reagent (100 μg/mL in acetonitrile) were applied and mixed using a pipette tip. In the next mini-well, 5 μL of CAX-DZ reagent and 10 μL of the raspberry sample were applied and mixed well using a pipette tip. The plate was then kept under UV light at 360 nm for 5 min. To both mini-wells was added 5 μL of 50% ACN and a 2 μL aliquot was taken from each mini-well and transferred to a separate vial containing 50 μL of CHCA matrix. A 2 μL aliquot was taken from each vial and diluted with 50 μL of CHCA matrix. About 0.7 μL of this mixture was taken per spot onto MALDI-TOF-MS plate and analyzed using MALDI-TOF-TOF-MS. The results of the experiments are shown in FIG. 10.

Example 7

Labeling and Analysis of Human Urine

Figure 11:
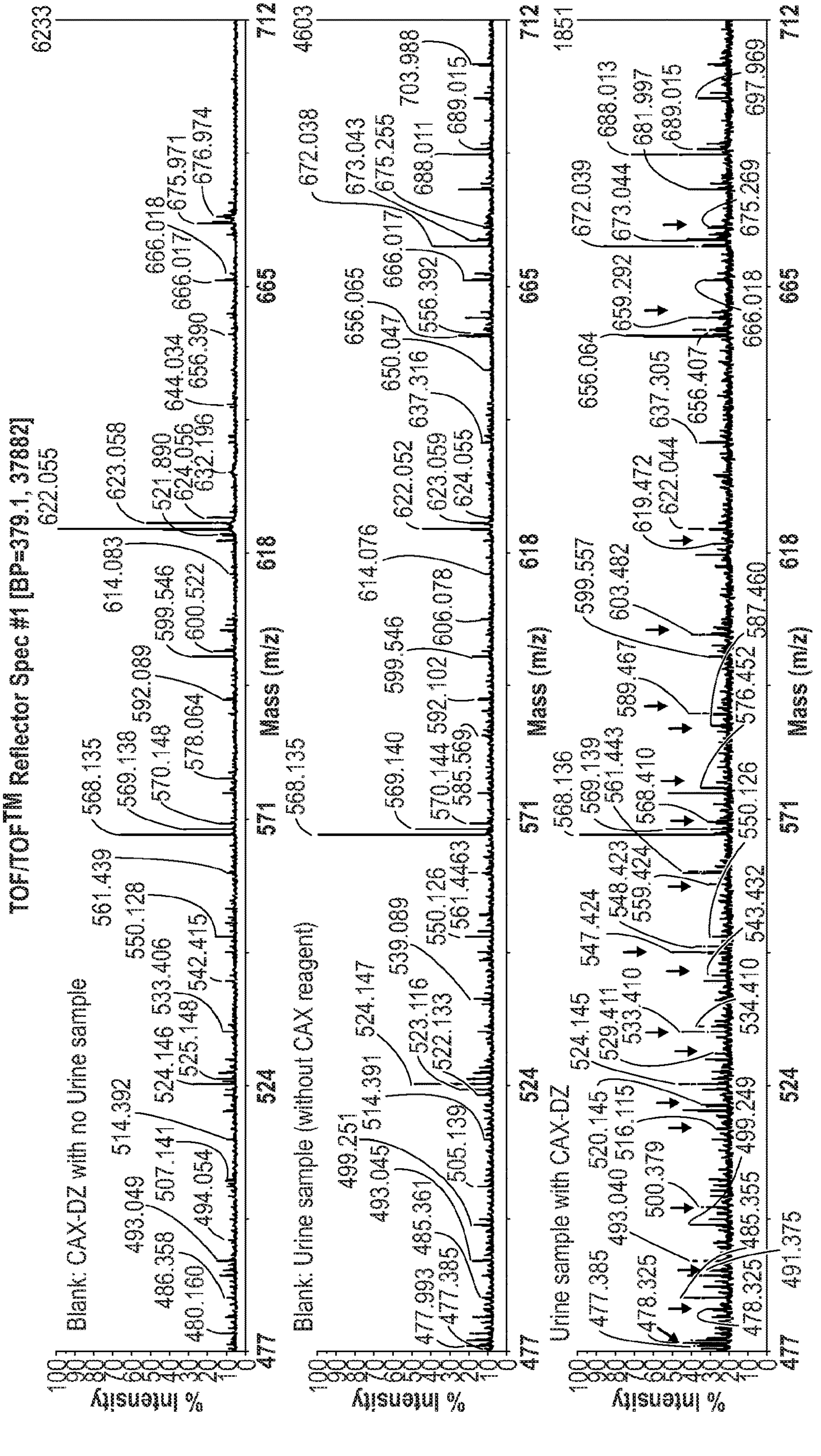
FIG. 11 shows mass spectra demonstrating CAX-DZ/UV/MALDI-TOF-MS detection of human urine metabolites.

In a mini-well 10 μL of water and 5 μL of CAX-DZ reagent (5 μg/mL in acetonitrile) were applied and mixed using a pipette tip. In the next mini-well, 5 μL of CAX-DZ reagent and 10 μL of urine sample were applied and mixed well using a pipette tip. The plate was kept under UV light for 5 min. To both mini-wells was added 5 μL of 50% ACN and a 2 μL aliquot was taken from each mini-well and transferred to a separate vial containing 50 μL of CHCA matrix. A 2 μL aliquot was taken from each vial and diluted with 50 μL of CHCA matrix. About 0.7 μL of this mixture was taken per spot on MALDI-TOF-MS plate and analyzed using MALDI-TOF-TOF-MS. The results of the experiments are shown in FIG. 11.

Example 8

Labeling and Analysis of Gasoline

Figure 12:
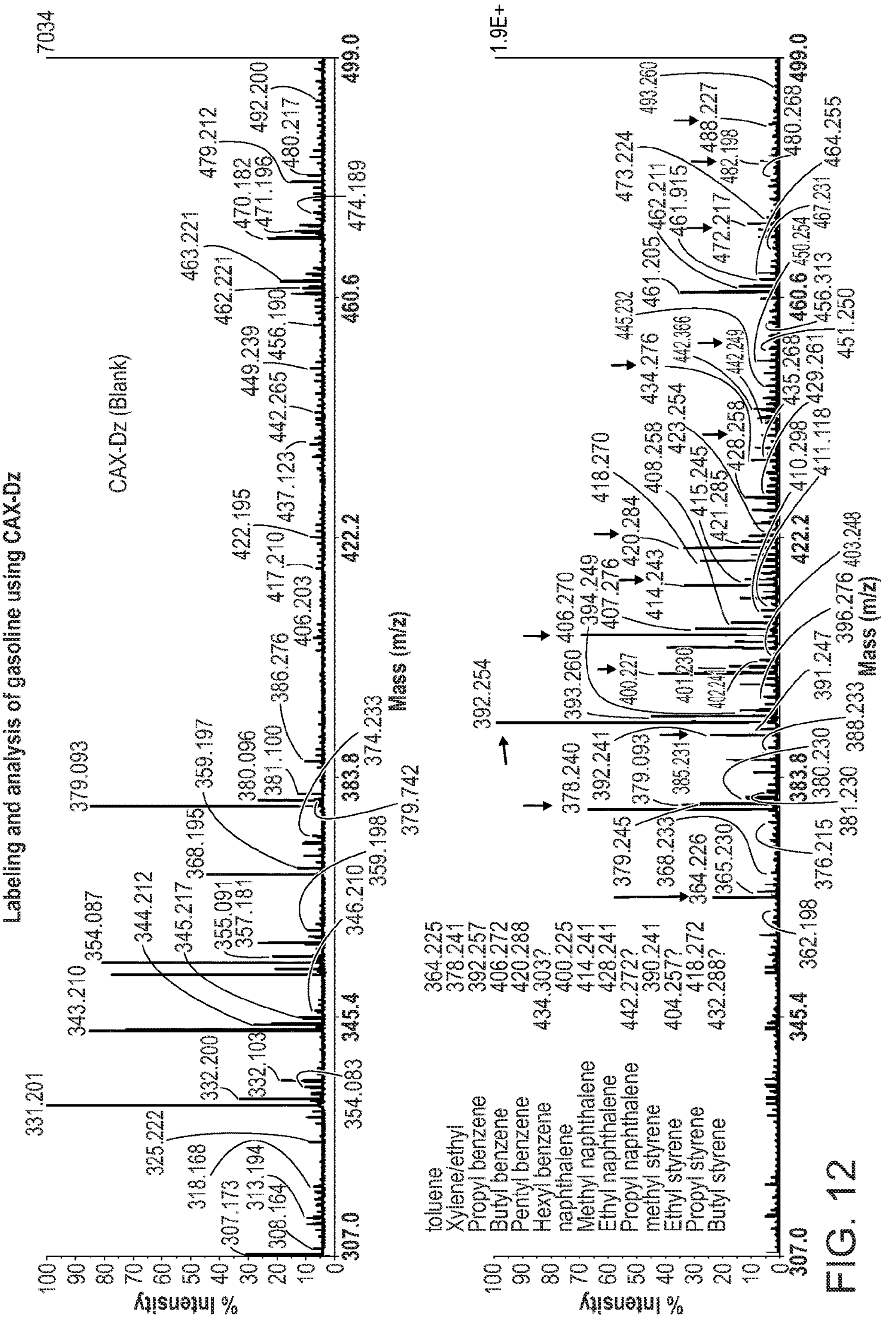
FIG. 12 shows mass spectra demonstrating CAX-DZ/UV/MALDI-MS detection of chemicals in gasoline.

In a mini-well 10 μL of water and 5 μL of CAX-DZ (2 mg/mL) reagent were added and mixed using a pipette tip. In the next mini-well 5 μL of CAX-DZ reagent and 10 μL of gasoline sample (added 1 μL at a time) were added and mixed well using a pipette tip. The plate was then kept under UV light at for 2 min. To the mini-wells was added 10 μL of 70% ACN and the contents of each mini-well were transferred to a separate vial containing 100 μL of CHCA matrix. About 0.7 μL of this was taken per spot on MALDI-TOF-MS plate and analyzed using MALDI-TOF-TOF-MS. The results of the experiments are shown in FIG. 12.

Example 9

Labeling and Analysis of a Sugar Mixture (Glucose, Fructose and Galactose)

Figure 4:
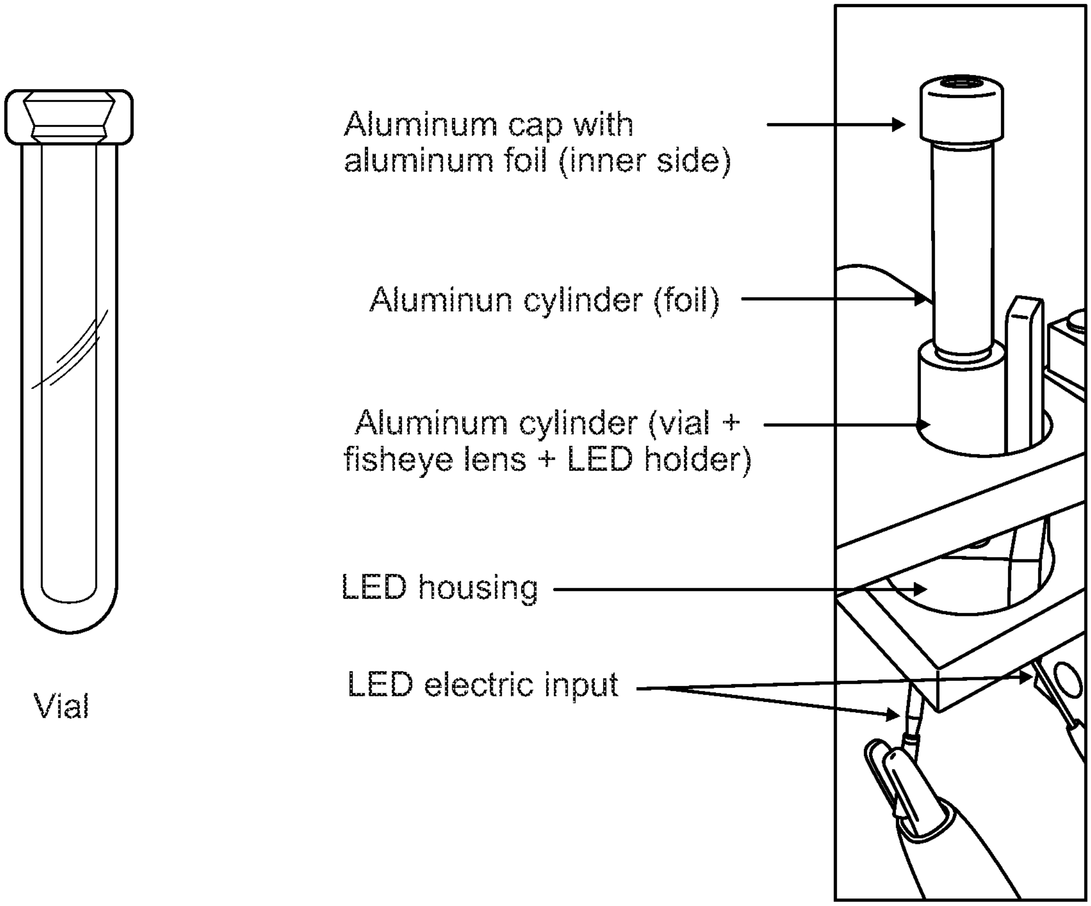
FIG. 4 shows assembly of the labeling reaction apparatus using aluminum: the lower section hosts the LED, the middle section supports the pair of fisheye lenses, and the upper chamber accommodates one or more reaction vials enclosed within a reflective cover.
Figure 13:
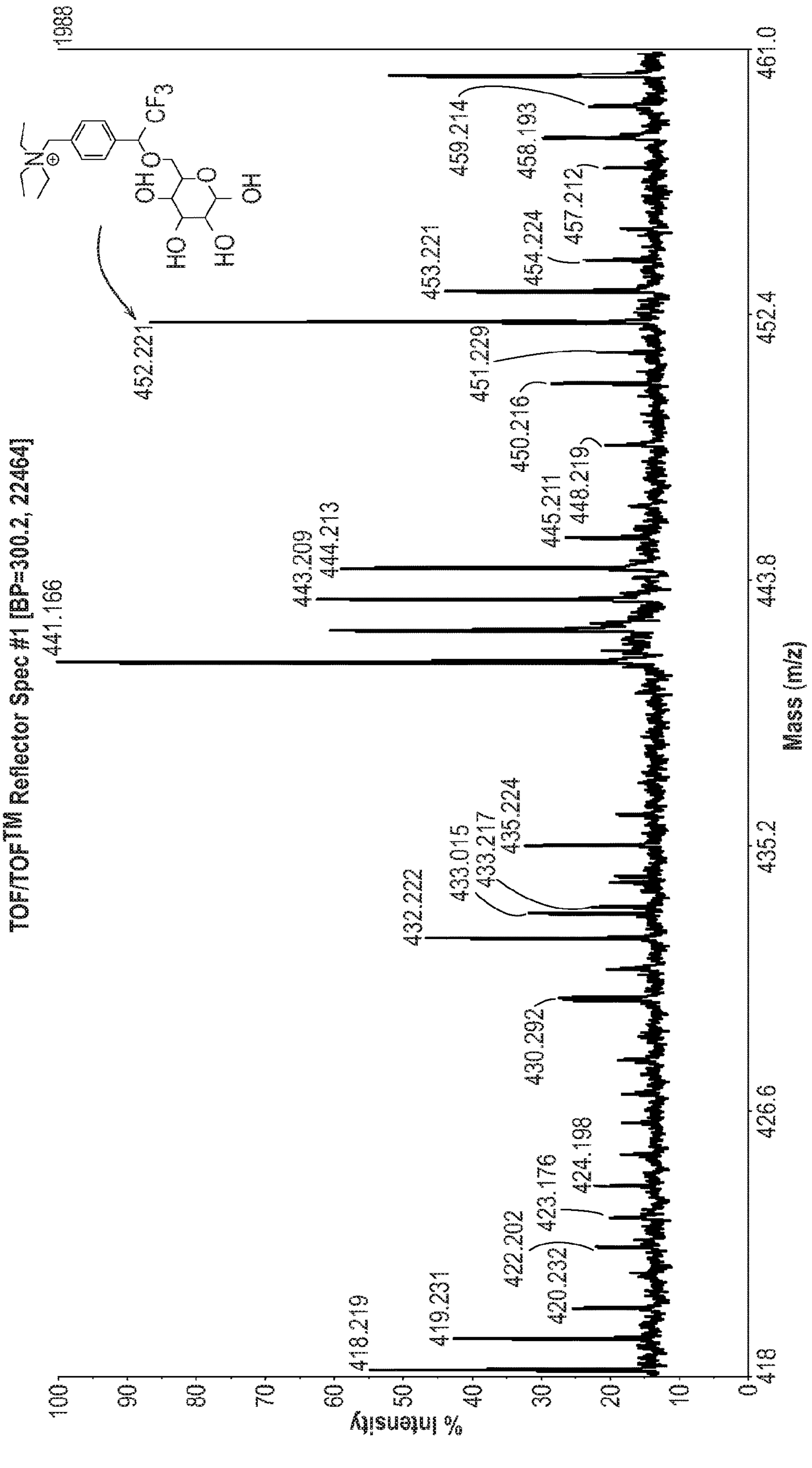
FIG. 13 shows a mass spectrum demonstrating Detection of the sugar mixture consisting of galactose, glucose and fructose isomers by CAX-DZ/LED/MALDI-TOF-MS. Exact mass of each CAX-sugar: 452.225; observed: 452.221.
Figure 14:
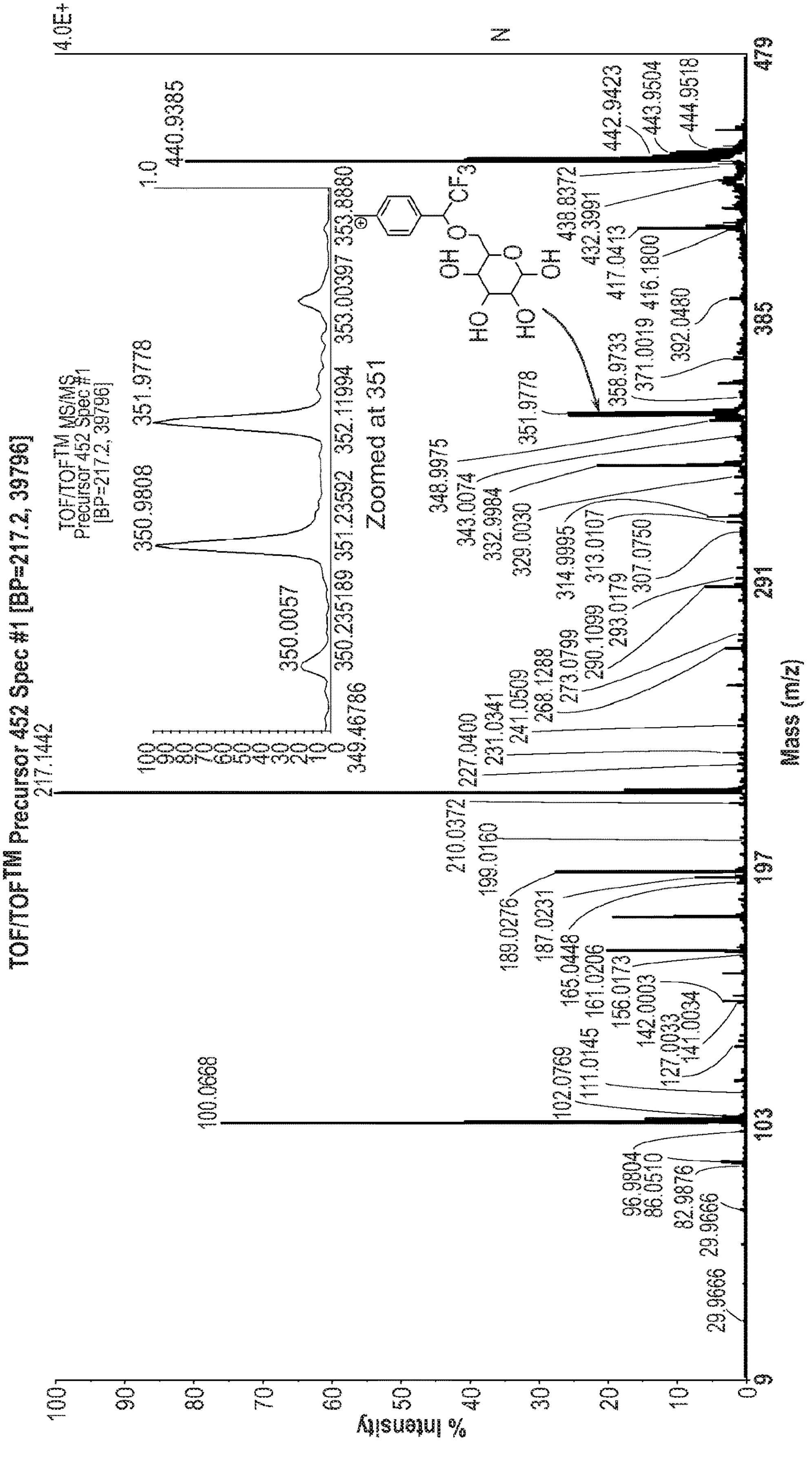
FIG. 14 shows a MALDI-TOF/TOF-MS/MS mass spectrum at m/z 452 (mass of precursor ion) of CAX-labeled sugar mixture (galactose, glucose and fructose).

Five microliters of 50 μL CAX-DZ stock solution (40 μL of CAX-DZ, 1 mg/mL in ACN) and 10 μL of a sugar mixture (glucose, fructose and galactose, each 100 μg/mL in 90% ACN) were combined in a vial and dried under vacuum. To the resulting residue was add 10 μL of $C_6F_6$. This vial was enclosed in a stainless steel cylinder (mirror finished) and a UV LED was placed right below the bottom of the vial, as shown in FIG. 4. The vial was exposed to the LED light for 20 min, the volatiles were removed under vacuum, the residue was replenished with 10 μL of CHCA matrix, vortexed, and 0.7 μL of the resulting solution was loaded per spot (3 spots) on a MALDI-TOF-MS plate, and MALDI-TOF-MS data along with corresponding TOF/TOF data were acquired. The results of the experiments are shown in FIGS. 13 and 14.

Example 10

Labeling and Analysis of Acebutolol

Figure 2:
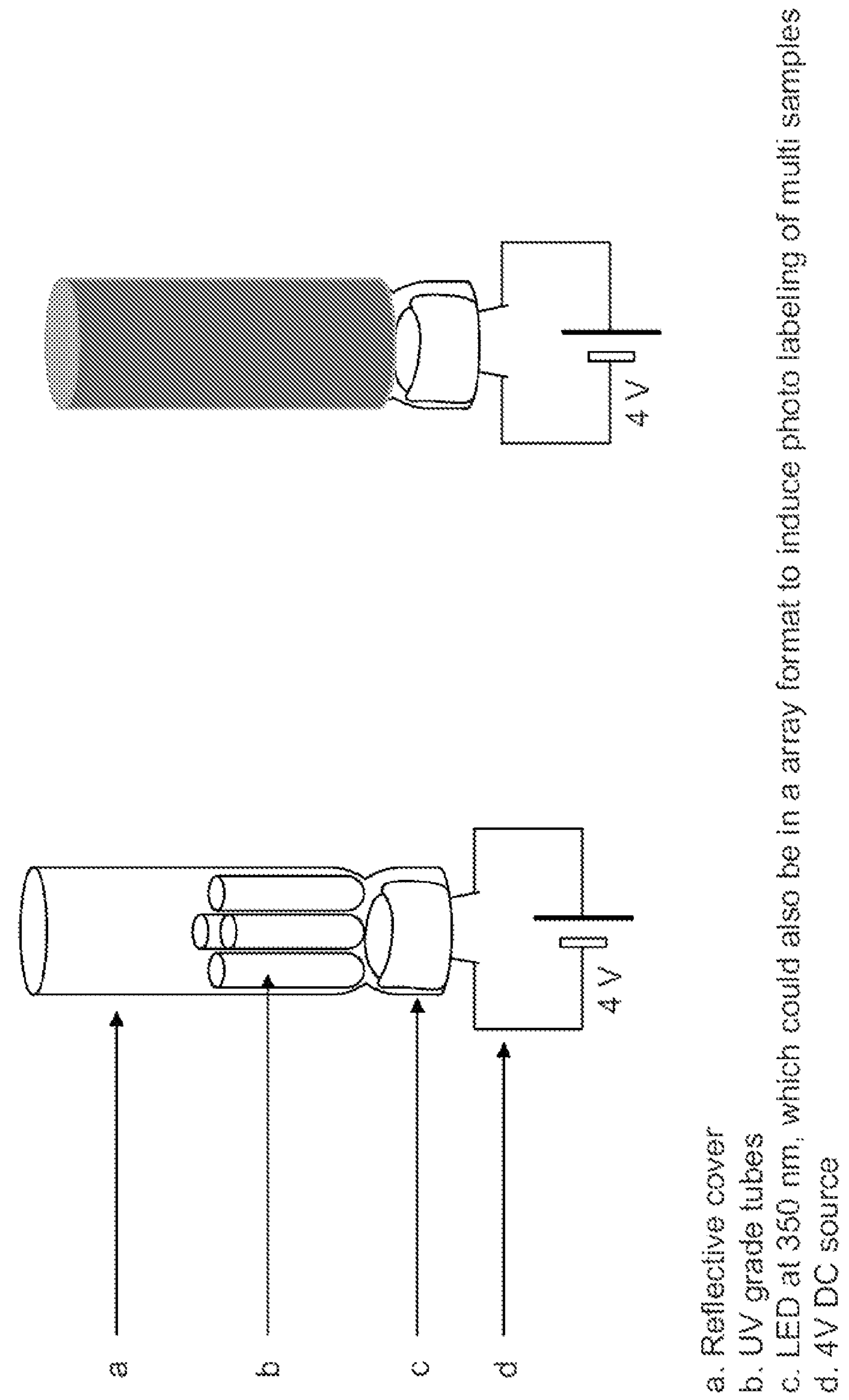
FIG. 2 shows a schematic representation of performing the CAX-DX labeling reaction over a button LED using a reflective holder.
Figure 3:
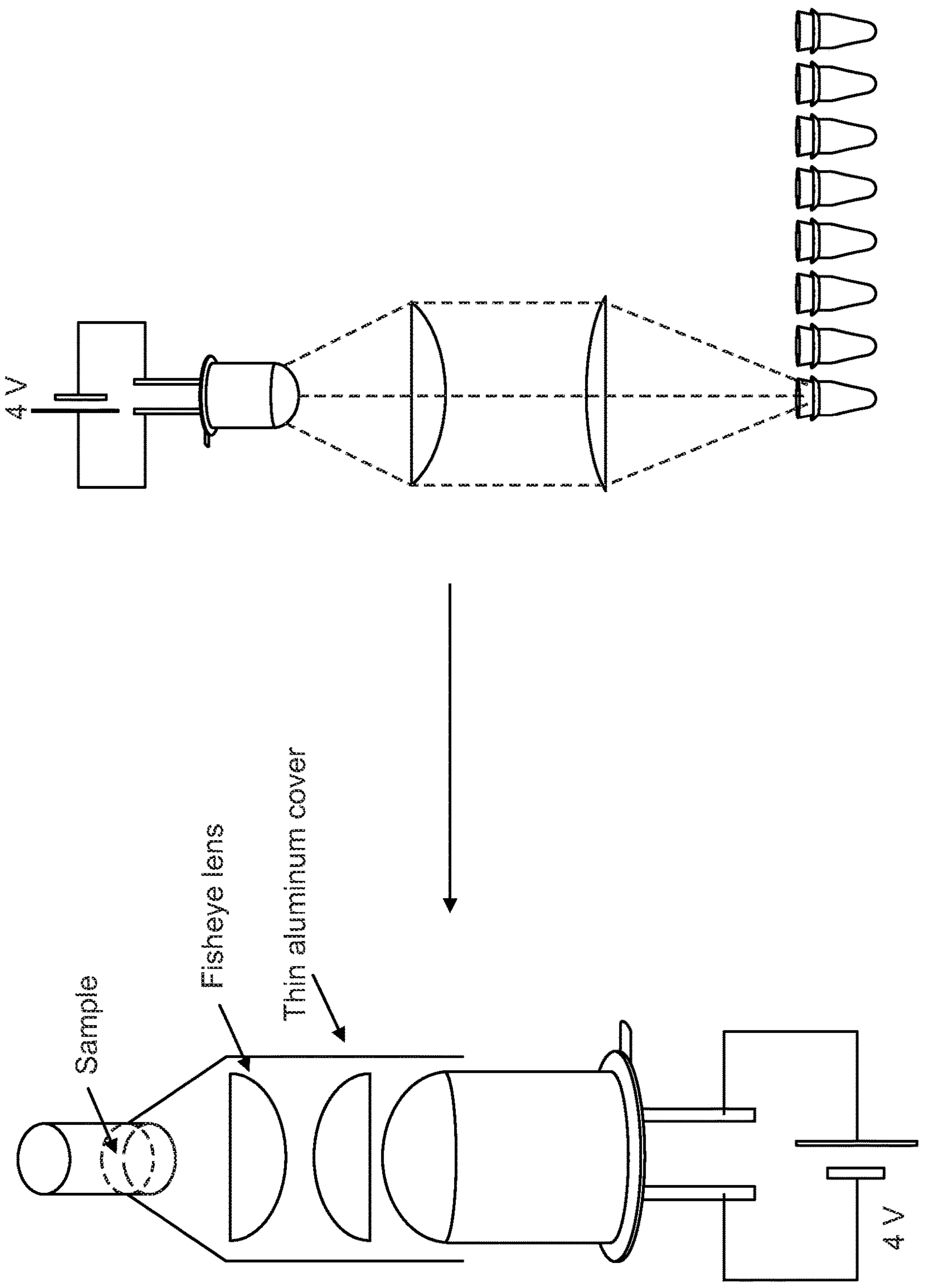
FIG. 3 shows a schematic representation of performing the labeling reaction by focusing the LED output with a pair of short focal length lenses (fisheye lenses) in order to focus the UV photons to a small spot and to induce the labeling reaction at higher photon density from the above. A pair of fisheye lenses can also be used to focus the LED output and perform the labeling reaction from the below as illustrated by the left diagram.
Figure 16:
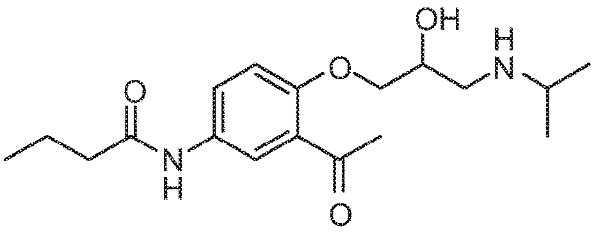
FIG. 16 shows a table demonstrating that acebutolol is labeled in high yield via reaction with CAX-DZ/LED.
Figure 17:
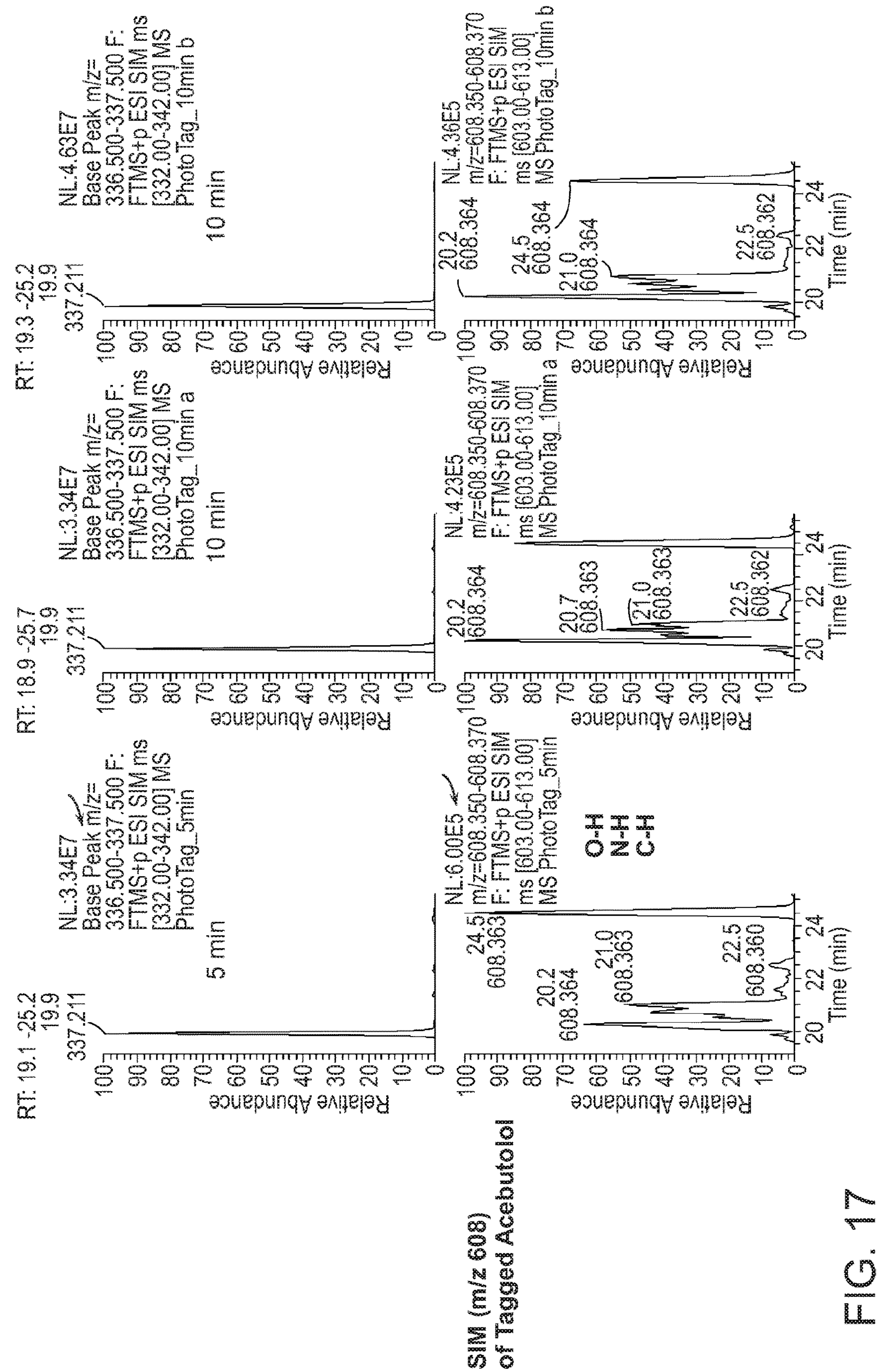
FIG. 17 shows mass spectra demonstrating pattern of peaks formed when acebutolol is carbene-labeled (CAX-DZ/LED) in triplicate, and then analyzed by liquid chromatography/mass spectrometry after 5 (one sample) and 10 minutes of reaction (two samples). The upper mass chromatograms show some residual, unreacted acebutolol in all of the samples (selected ion monitoring, m/z 337, chromatograms extracted from full scan data). The lower mass chromatograms show detection of labeled acebutolol in all of the same samples (selected ion monitoring, m/z 608, chromatograms extracted from full scan data). Overall, as seen by in the lower chromatograms, the acebutolol molecules are each labeled once by the carbene mass tag, but distributed over at least 8 major attack sites. This gives a unique signature of peaks from acebutolol.
Figure 18:
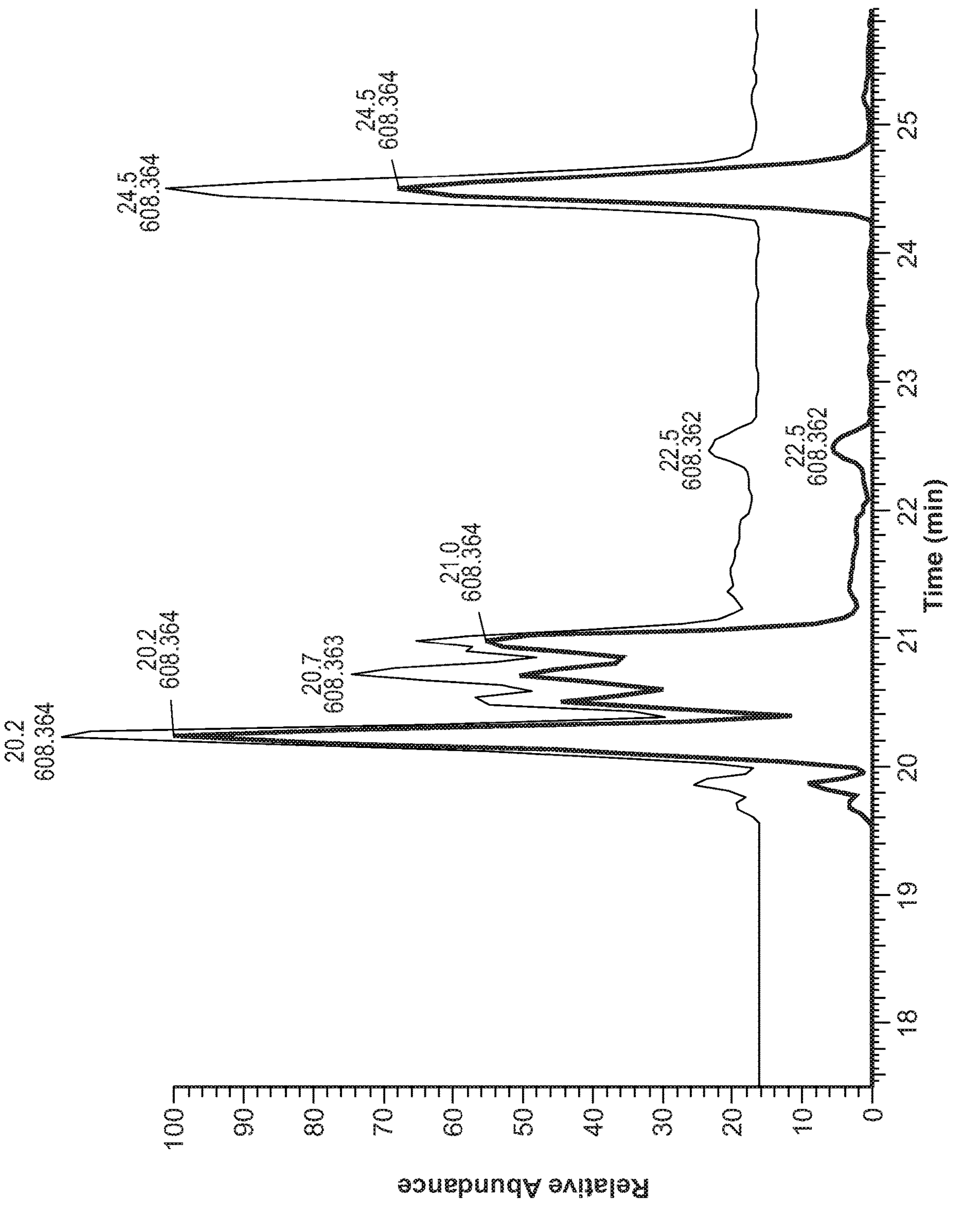
FIG. 18 shows superimposed, expanded ion chromatograms of the duplicate data from the two lower chromatograms at 10 minutes in FIG. 17, more clearly showing the high reproducibility of the signatures.

Five microliters of 50 μL CAX-DZ stock solution (40 μL of CAX-DZ, 1 mg/mL in ACN) and 10 μL of acebutolol (100 μg/mL in 90% ACN) were combined in each of four capillary vials and volatiles were removed under vacuum. To each vial was added 10 μL of $C_6F_6$. The vials were enclosed in glass cylinder made by cutting a Pasteur pipet, which in turn was enclosed in a stainless steel cylinder (mirror finished). A UV LED was placed right below the bottom of this cluster of vials as shown in FIG. 2. The vials were exposed to LED light and processed as described in Example 10. The results of the experiments are shown in FIGS. 16-18.

Example 12

Labeling and Analysis of 1-propanol

Figure 15:
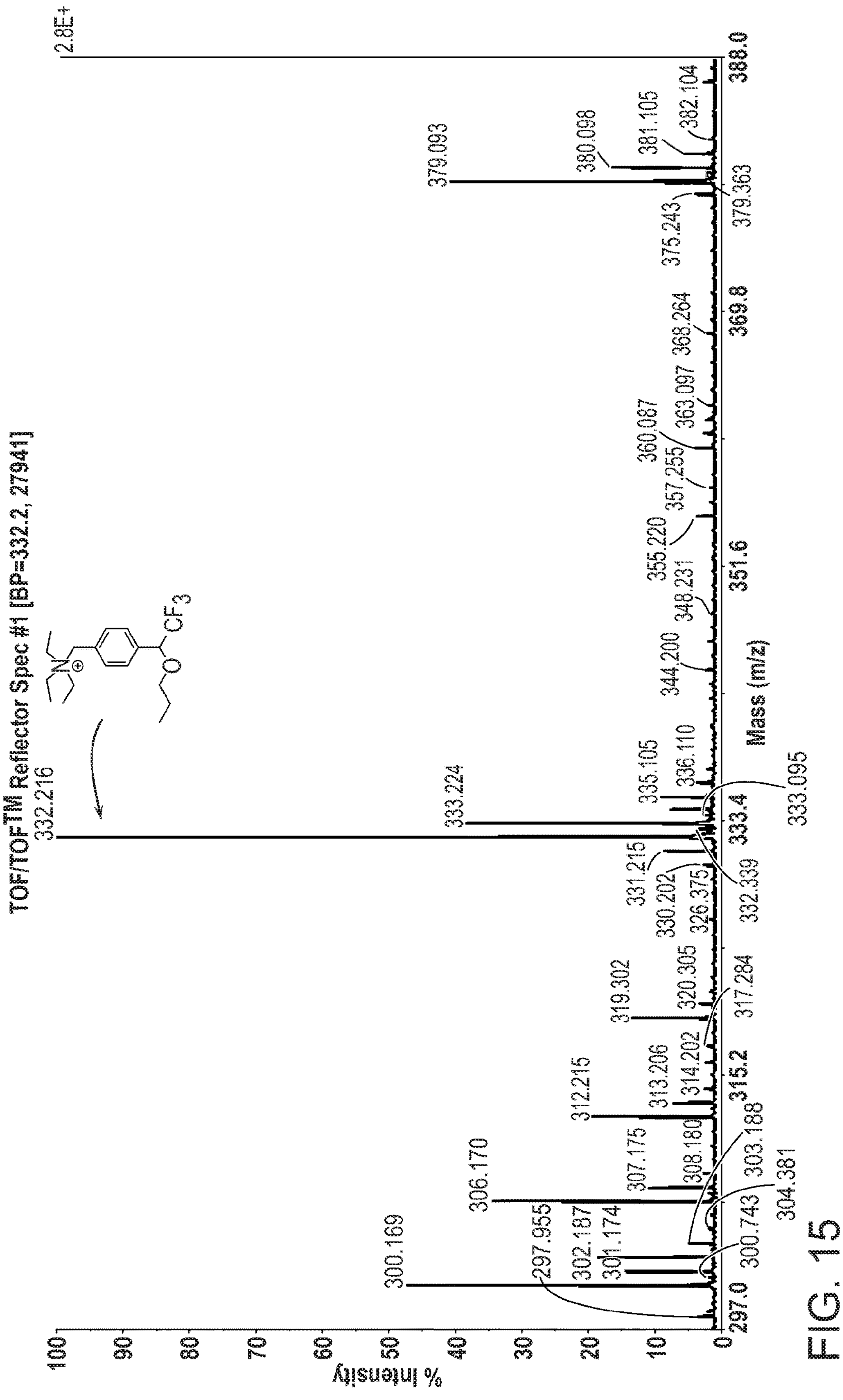
FIG. 15 shows a mass spectrum demonstrating detection of 1-propanol by CAX-DZ/LED/MALDI-TOF-MS. Exact mass of CAX-propanol: 332.220, observed 332.216.

Five microliters of 50 μL CAX-DZ stock solution (40 μL of CAX-DZ, 1 mg/mL in ACN) were placed in a reaction vial and volatiles were removed under vacuum. To this residue was added 9 μL of $C_6F_6$ and 1 μL of propanol. The vial was enclosed in a stainless steel cylinder (mirror finished) and a UV LED was placed right below the bottom of this vial as shown in FIG. 4. The vial was exposed to LED light and processed as described in Example 10. The results of the experiments are shown in FIG. 15.

Example 13

Measurement of Alcohol in Breath by CMT

A tube of plastic, glass or metal is set up having the size of a cigarette filter or cigarette and containing an adsorbent for alcohol such as cellulose (e.g. cotton), nylon, silica, bonded (e.g. alkyl, aryl) silica, sand, or Tenax™. A CMT reagent such as DEA-DZ can be present or added later. One or more calibration standards such as $D_2O$, butanol, ethylene glycol, cyclooctane, naphthalene, $CD_3CD_2OH$, or perfluorobutanol are present in the tube. One calibration standard can monitor the breath volume passing through the tube by being partly swept out by the breath. Another calibration standard stays in the tube as the breath passes through and thereby serves as an internal standard to calibrate the ethanol measurement. This calibration refers to both the signals for the labeled ethanol and the labeled volume standard. In storage prior to use, the tube is sealed at both ends by a metal foil or metal-backed foil or plastic sheet or plastic cap with an inner metal foil. To measure ethanol in breath, the two seals are removed and the subject breathes through the tube. The tube can be cooled as by a thermoelectric module or cold pack during this step to increase capture of the ethanol. During this step, the amount of breath flowing through the device can be measured with a balloon or a flowmeter, as a second option instead of the above calibration standard for breath volume. The caps are put back on the tube until the alcohol and calibration standard(s) in the tube are measured. Measurement of the ethanol can then take place in two types of ways.

Direct Measurement. The tube is interfaced to a MS and/or IMS system and heated. The heat causes the DEA-DZ to discharge nitrogen, yielding a carbene that reacts both with the ethanol and the calibration standards. The resulting labeled products of ethanol and calibration standards are flushed out of the tube by a gas such as nitrogen into an MS and/or IMS system for measurement. Alternatively, a solvent can be added to the tube; the tube is heated to give the carbene labeling reaction; and the solvent containing the labeled products is directed to an MS and/or IMS system.

Indirect Measurement. A solvent is used to elute the ethanol and calibrations standard(s), which are then, perhaps after evaporation, reacted with DEA-DZ by applying energy, where the DEA-DZ either has been added either before after the eluent comes out of the tube. A unique pattern of 3 peaks in terms of retention time and relative intensity, providing signature detection, is observed for labeled ethanol, and quantitation is provided by comparing the intensity of the labeled products from ethanol and the calibration standard (s).

Example 14

Measurement of Metabolites in Breath by CMT

Metabolites can be measured in breath by CMT in the same way as for ethanol. Different internal standards can be used. The breath also can be collected into a cup or onto a piece of filter paper. The cup can contain a trapping solvent such as isopropanol and can be cooled with ice.

INCORPORATION BY REFERENCE

All U.S. patents and U.S. and PCT patent application publications mentioned herein are hereby incorporated by reference in their entirety as if each patent or publication was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A compound consisting of an $R_1$-aryl$_1$—$CHR_2$—$NR_3R_4R_5$ (RACN) moiety, a single polyfluoroalkyldiazirine (PFAD) group, and a counterion;

wherein:

$R_1$ is H, $XCH_3$, $XCH_2CH_3$, $CH_2XCH_3$, $CH_2XCH_2CH_3$, or a group that connects to the PFAD group;

X is O or S;

aryl is phenyl, pyridyl, or pyrimidyl;

$R_2$ is H or a group that connects to the PFAD group;

$R_3$ is H or an alkyl or aryl group having 6 or fewer carbon atoms;

each of $R_4$ and $R_5$ is an alkyl or aryl group having 6 or fewer carbon atoms; and the counterion is selected from the group consisting of bromide, chloride, fluoride, nitrate, acetate, trifluoroacetate, pivalate, bicarbonate, arsenite, dihydrogenarsenate, hexafluoroarsenate, perfluorobutane sulfonate, perfluorohexane sulfonate, perfluorooctane sulfonate, perchlorate, cyanide, tetrafluoroborate, trichlorostannate, trifluorosulfonate, and pentafluorophenolate.

2. The compound of claim 1, wherein $R_1$ is ortho to $CHR_2$—$NR_3R_4R_5$.

3. The compound of claim 1, wherein aryl$_1$ is phenyl.

4. The compound of claim 1, wherein the perfluoroalkyl moiety of the PFAD group is selected from the group consisting of $CF_3$, $C_2F_5$, $C_3F_7$, and $C_4F_9$.

5. The compound of claim 1, wherein the PFAD group is directly attached to aryl$_1$.

6. The compound of claim 1, wherein $R_1$ is a group that connects to the PFAD group which is represented by the following structural moiety:

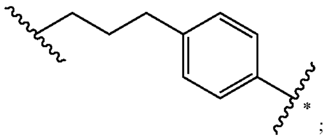 [SMILES: *CCCc1ccc(*)cc1]

;

and

* indicates the point of attachment to PFAD group.

7. The compound of claim 1, wherein $R_1$ is a group that connects to the PFAD group which is represented by the following structural moiety:

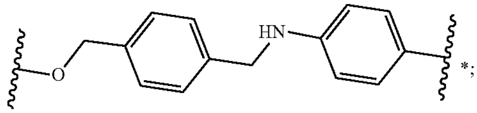 [SMILES: *OCc1ccc(CNc2ccc(*)cc2)cc1]

;

and * indicates the point of attachment to PFAD group.

8. The compound of claim 1, wherein the counterion is selected from the group consisting of bromide, chloride, fluoride, nitrate, acetate, trifluoroacetate, perfluorobutane sulfonate, perfluorohexane sulfonate, pentafluorophenolate, bicarbonate, and arsenite.

9. The compound of claim 1, wherein the compound is

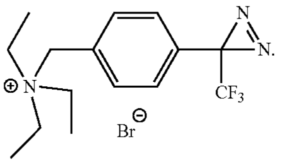 [SMILES: CC[N+](CC)(CC)Cc1ccc(C2(C(F)(F)F)N=N2)cc1 ; [Br-]]

.

10. A compound represented by structural formula (I)

(I)

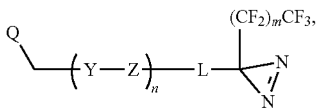

, wherein, independently for each occurrence,

Q is —$(NR^6R^7R^8)^+X^-$;

X is halide, $NO_3$, $OC(O)CH_3$, $OC(O)C(CH_3)_3$, $OC(O)CF_3$, $HCO_3$, $AsO_2$, $H_2AsO_4$, $AsF_6$, $SO_3(C_4F_9)$, $SO_3(C_6F_{13})$, $SO_3C_8F_{17}$, $ClO_4$, CN, $BF_4$, $SnC_{13}$, $CF_3SO_3$, or $C_6F_5O$;

$R^6$, $R^7$, $R^8$ is each independently $C_{1-6}$ alkyl or $C_6$aryl;

Y is phenyl, pyridyl, or pyrimidyl;

Z is —$(CH_2)A(CH_2)$k—;

L is —$(CH_2)A(CH_2)_k$— or absent;

A is O, S, or NH;

1 is 0 to 2;

k is 0 to 2;

m is 0 to 10; and n is 1 to 3.

11. A compound selected from

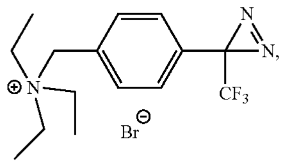

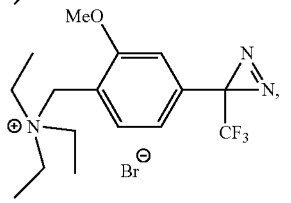

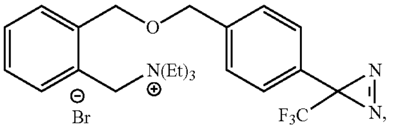

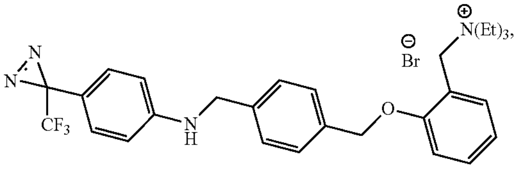

and

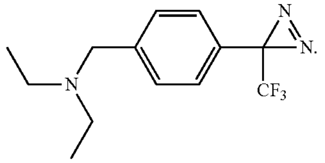

12. A method for detecting one or more analytes in a sample, comprising:

a) combining the sample and a reagent mixture, wherein the reagent mixture comprises a diazirine precursor mass tag reagent, and wherein the diazirine precursor mass tag reagent is a compound of claim 1, thereby generating an analyte mixture;

b) exposing the analyte mixture to a source of energy, thereby providing a derivatized analyte mixture; and c) analyzing the derivatized analyte mixture, thereby detecting the one or more analytes.

13. The method of claim 12, wherein the reagent mixture further comprises a solid support.

14. The method of claim 13, wherein a carbene reagent is deposited on the solid support.

15. The method of claim 12, wherein the source of energy is selected from the group consisting of UV photons, LED photons, UV LED photons, heat, laser photons, electrons, photons from fluorescence energy transfer, plasma, a metastable compound, an energy-releasing molecule, a vibrationally-activated molecule, and a combination thereof.

16. The method of claim 12, wherein the derivatized analyte mixture further comprises one or more calibration standards.

17. The method of claim 12, further comprising treating the derivatized analyte mixture with a carbene-reactive scavenger agent before step c), thereby generating a scavenged carbene reagent.

18. The method of claim 17, further comprising removing the scavenged carbene reagent from the derivatized analyte mixture before step c).

19. The method of claim 12, wherein analyzing the derivatized analyte mixture is done by an analytical method selected from the group consisting of ion mobility mass spectrometry, liquid chromatography-electrospray ionization mass spectrometry, infusion-electrospray ionization mass spectrometry, and matrix-assisted laser desorption ionization mass spectrometry.

20. The method of claim 19, wherein the analytical method is matrix-assisted laser desorption ionization mass spectrometry.

* * * * *